United States Patent
van der Stelt et al.

(10) Patent No.: US 8,143,246 B2
(45) Date of Patent: Mar. 27, 2012

(54) 1-(4-(PYRIDIN-2-YL)BENZYL) IMIDAZOLIDINE-2,4-DIONE DERIVATIVES

(75) Inventors: Marcelis van der Stelt, Oss (NL); Joseph Maria Gerardus Barbara Cals, Oss (NL); Johannes Petrus Gerardus Klomp, Oss (NL)

(73) Assignee: MSD OSS B.V., Oss (NL)

( * ) Notice: Subject to any disclaimer, the term of this patent is extended or adjusted under 35 U.S.C. 154(b) by 220 days.

(21) Appl. No.: 12/628,538

(22) Filed: Feb. 15, 2010

(65) Prior Publication Data
US 2010/0144724 A1 Jun. 10, 2010

Related U.S. Application Data

(60) Provisional application No. 61/119,211, filed on Dec. 2, 2008.

(30) Foreign Application Priority Data

Dec. 2, 2008 (EP) .................................. 08170480

(51) Int. Cl.
C07D 417/14 (2006.01)
C07D 401/14 (2006.01)
C07D 413/14 (2006.01)
C07D 405/14 (2006.01)
A61K 31/445 (2006.01)
A61K 31/541 (2006.01)

(52) U.S. Cl. ................ 514/227.8; 544/131; 544/58.6; 546/194; 514/318; 514/235.8

(58) Field of Classification Search ............ 514/227.8, 514/318, 235.8; 544/131, 58.6
See application file for complete search history.

(56) References Cited

FOREIGN PATENT DOCUMENTS

| WO | WO2001/056996 | 8/2001 |
|----|---------------|--------|
| WO | WO2004/018433 | 3/2004 |
| WO | WO2007/070760 | 6/2007 |
| WO | WO2010/063666 | 6/2010 |

OTHER PUBLICATIONS

Govaerts et al. European Journal of Pharmacology 495 (2004), 43-53.*
International Search Report for PCT/EP2009/066156 filed Jan. 12, 2009 mailed on Jan. 19, 2010; 4 pages.
Written Opinion for PCT/EP2009/066156 filed Jan. 12, 2009 mailed on Jan. 19, 2010; 5 pages.
Govaerts Sophie, J. et. al.; "Characterization of the pharmacology of imidazolidinedione derivatives at cannabinoid CB1 and CB2 receptors", European Journal of Pharmacology; vol. 495, No. 1; Jul. 8, 2004; pp. 43-53.
International Search Report for PCT/EP2009/066030 filed Nov. 30, 2009 mailed on May 2, 2010; 4 pages.

* cited by examiner

Primary Examiner — Kahsay T Habte
(74) Attorney, Agent, or Firm — Keith D. MacMillan; Gerard M. Devlin

(57) ABSTRACT

The invention relates to 1-(4-(pyridin-2-yl)benzyl)imidazolidine-2,4-dione derivative having the general Formula I Formula I

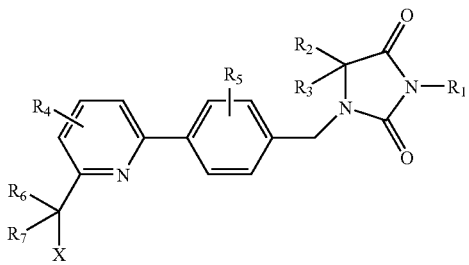

wherein $R_1$ is H, $(C_{1-6})$alkyl (optionally substituted with oxo, $(C_{1-3})$alkyloxy, $(C_{1-3})$alkyloxycarbonyl, halogen or CN), $(C_{3-6})$ cycloalkyl or $(C_{3-6})$cycloalkyl$(C_{1-3})$alkyl, each cycloalkyl ring optionally comprising a heteroatom selected from O and S; $R_2$ and $R_3$ are independently H or $(C_{1-3})$alkyl; or $R_2$ and $R_3$ form together with the carbon atom to which they are bound a $(C_{3-5})$cycloalkyl group; $R_4$ is H or 1 to 3 F substituents; $R_5$ is H or 1 to 4 F substituents; $R_6$ and $R_7$ are independently H or F; X represents $R_8$, $OR_8$, $NR_8R_9$,

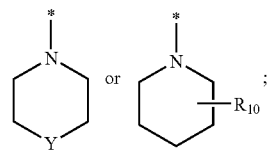

$R_8$ is $(C_{5-7})$cycloalkyl optionally comprising a heteroatom selected from O, S, SO and $SO_2$; $R_9$ is H or $(C_{1-4})$alkyl; $R_{10}$ represents 1-3 substituents independently selected from H, $(C_{1-3})$alkyl, halogen, oxo, CN and $CF_3$; Y is $CF_2$, O, S, SO or $SO_2$; or a pharmaceutically acceptable salt thereof, to pharmaceutical compositions comprising the same, as well as to the use of said 1-(4-(pyridin-2-yl)benzyl)imidazolidine-2,4-dione derivatives in the treatment of pain such as for example peri-operative pain, chronic pain, neuropathic pain, cancer pain and pain and spasticity associated with multiple sclerosis.

13 Claims, 1 Drawing Sheet

Von Frey Threshold (g)
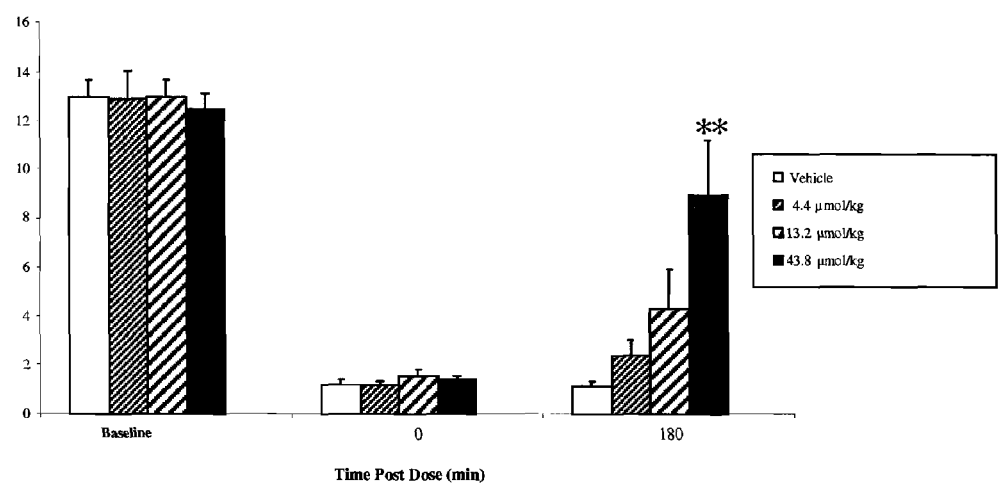

1-(4-(PYRIDIN-2-YL)BENZYL) IMIDAZOLIDINE-2,4-DIONE DERIVATIVES

This application is a non-provisional application that claims priority under 35 U.S.C. §119(e) of provisional application U.S. Ser. No. 61/119,211 filed Dec. 2, 2008, the contents of which are hereby incorporated by reference in its entirety.

BACKGROUND

The present invention relates to 1-(4-(pyridin-2-yl)benzyl)imidazolidine-2,4-dione derivatives, to pharmaceutical compositions comprising the same and to the use of these 1-(4-(pyridin-2-yl)benzyl)imidazolidine-2,4-dione derivatives in therapy, especially in the treatment of pain.

Pain is an unpleasant sensory and emotional experience associated with actual or potential tissue damage. Pain can be nociceptive or neuropathic in origin. Pain experienced as a consequence of arthritis is generally nociceptive in nature, caused by inflammation of tissue and stimulation of nociceptors. Major indications driving prevalence of nociceptive pains are low back pain, osteoarthritis, post-operative pain, and cancer-related pain. Major unmet needs for nociceptive pain are for improved efficacy and fewer side effects. The chronic pain market is currently dominated by non-steroidal anti-inflammatory drugs (NSAIDs) and cyclo-oxygenase COX-2 inhibitors. NSAIDs provide adequate analgesia to relieve mild to moderate pain and usually have greater effectiveness in inflammatory pain. Individual NSAIDs vary in their efficacy, and these variations are partly determined by differing COX-1/COX-2 selectivities. Consequently, patients may require to be treated with several different drugs before their pain is adequately treated. Side effects associated with drug therapy are an important factor in treatment choice, especially as many pain syndromes are long-term chronic conditions.

The most common side effects of NSAIDs are constipation and indigestion; most anti-inflammatory drugs are acidic in nature and promote acid production in the stomach. Other, serious side effects are gastrointestinal complications such as gastric ulcers, mucosal damage and peptic erosion. NSAIDs are thought to account for as many as 107,000 hospitalizations and 16,500 deaths due to ulcer complications in the US each year (Singh, *Recent considerations in nonsteroidal anti-inflammatory drug gastropathy*. Am. J. Med., 1998, 105: 31S-38S). Whilst COX-2 inhibitors have an improved gastrointestinal side effect profile, their use has been associated with increased risk of myocardial infarction and stroke and increased risk of hypertension.

Neuropathic pain, defined as chronic pain caused by injury, disease or dysfunction of the nervous system, is present in ~1% of the population; the largest patient populations include those with painful diabetic peripheral neuropathy, and those with neuralgia that persists after an attack of herpes zoster (post-herpetic neuralgia). It is characterized by a complex combination of symptoms, including spontaneous pain that can occur in the absence of tissue damage. Patients suffering from neuropathic pain also have increased sensitivity both to stimuli normally perceived as painful (hyperalgesia), as well as to stimuli that do not normally provoke pain (allodynia). These symptoms are often refractory to conventional analgesic therapies, with most patients achieving incomplete relief of their symptoms. Currently, antidepressants, anticonvulsants and opioids remain first-line treatment, with gabapentin as the gold standard. All of these drugs have significant side-effects that are dose limiting. In addition, efficacy is a considerable problem in the neuropathic pain market with current treatments showing a maximum of 50% reduction in overall pain scores from baseline. Consequently, there remains an unmet medical need for agents that have higher efficacy/responder rate, and with reduced side-effects compared with currently used drugs.

Emerging clinical evidence, as well as anecdotal reports from patients self-medicating with cannabis, suggest that cannabinoid receptor agonists may have a role in treating pain (Fox A, Bevan S., *Therapeutic potential of cannabinoid receptor agonists as analgesic agents*. Expert Opin Investig Drugs, 2005, 14, 695-703). GW Sativex, a 1:1 ratio of $\Delta^9$-THC and cannabidiol in an oromucosal spray formulation that allows individualised dosing for the treatment of neuropathic pain has been launched by GW Pharmaceuticals. Clinical studies with Sativex have demonstrated efficacy in patients with intractable pain (chronic neuropathic pain, pain due to brachial plexus nerve injury, allodynic peripheral neuropathic pain and advanced cancer pain), rheumatoid arthritis and symptoms associated with multiple sclerosis (pain, spasticity, poor bladder control and disrupted sleep; (Barnes M P. 2006. *Sativex: clinical efficacy and tolerability in the treatment of symptoms of multiple sclerosis and neuropathic pain*. Expert Opin. Pharmacother. 7(5): 607-615).

Two types of cannabinoid receptors have been identified. The cannabinoid CB1 receptor is located primarily in the central nervous system (CNS; brain and spinal cord), but is also expressed by peripheral neurones and to a lower extent in other peripheral tissues. The cannabinoid CB2 receptor is mainly confined to the periphery, mostly in immune cells (Howlett, A. C. et al, International Union of Pharmacology. XXVII. *Classification of Cannabinoid Receptors*. Pharmacol. Rev. 54, 161-202, 2002). While the conventional CB1 receptor agonists and CB1/CB2 receptor agonists, such as tetrahydrocannabinol (THC) are highly effective in models of pain in animals, their therapeutic utility in man is limited by undesired CNS side-effects, such as psychoactive effects, and by abuse potential (Chapman, V. and Finn, D. P. "*Analgesic effects of cannabinoids: sites and mechanism of action*." Rev. Analg. 7, 25-39, 2003).

Recent literature evidence suggests that selective activation of the CB2 receptor may constitute a novel strategy for treating pain and inflammation without undesirable CNS side effects. (Guindon, J. and Hohmann, A., "*Cannabinoid CB2 receptors: a therapeutic target for the treatment of inflammatory and neuropathic pain*", Br. J. Pharmacol., 2008, 153, 319-334). Activation of the CB2 receptor was found to inhibit acute, inflammatory and neuropathic pain responses in animal models (Whiteside G. T., Lee G. P., Valenzano K. J. "*The role of the cannabinoid CB2 receptor in pain transmission and therapeutic potential of small molecule CB2 receptor agonists*, Current Med. Chem., 2007, 14, 917-936). CB2 knock-out mice studies also support a role for CB2 receptors in pain (Malan T P, Jr, Ibrahim M M, Lai J, Vanderah T W, Makriyannis A and Porreca F. *CB2 cannabinoid receptor agonists: pain relief without psychoactive effects*? Curr. Opin. Pharmacol. 2003; 3: 62-67).

The cellular mechanisms contributing to CB2-mediated antinociception are not yet clear, but it has been proposed that activation of CB2 receptors affects inflammatory pain indirectly via modulation of immune cell activity, resulting in decreased release of mediators at the local site of inflammation. In addition to a peripheral effect, recent publications suggest that CB2 receptor agonists can also interact with CB2 receptors expressed on peripheral neurons and activated microglia to modulate pain transmission. (Beltramo et al., 2006. *CB2 receptor-mediated antihyperalgesia: possible* direct involvement of neural mechanisms. Eur J Neurosci. 23(6):1530-80; Romero-Sandoval & Eisenach, 2007. *Spinal cannabinoid receptor type 2 activation reduces hypersensitivity and spinal cord glial activation after paw incision.* Anesthesiology 106(4):787-94).

In summary, CB2 receptor agonists may be suitable for the treatment of acute and chronic pain conditions, such as osteoarthritis, rheumatoid arthritis and acute post-operative pain and neuropathic pain. The absence of catalepsy with CB2 agonists in preclinical models shows promise for the treatment of acute and chronic pain without undesired CNS side effects Thus, there is a need for selective CB2 cannabinoid receptor agonists as therapeutic agents in the treatment of pain.

SUMMARY OF THE INVENTION

To this end the present invention provides a novel structural class of 1-(4-(pyridin-2-yl)benzyl)imidazolidine-2,4-dione derivative having the general Formula I

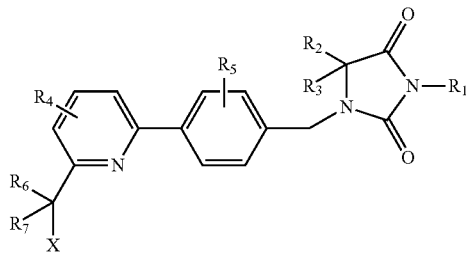

Formula I wherein
$R_1$ is H, $(C_{1-6})$alkyl (optionally substituted with oxo, $(C_{1-3})$alkyloxy, $(C_{1-3})$alkyloxycarbonyl, halogen or CN), $(C_{3-6})$cycloalkyl or $(C_{3-6})$cycloalkyl$(C_{1-3})$alkyl, each cycloalkyl ring optionally comprising a heteroatom selected from O and S;
$R_2$ and $R_3$ are independently H or $(C_{1-3})$alkyl; or
$R_2$ and $R_3$ form together with the carbon atom to which they are bound a $(C_{3-5})$cycloalkyl group;
$R_4$ is H or 1 to 3 F substituents;
$R_5$ is H or 1 to 4 F substituents;
$R_6$ and $R_7$ are independently H or F;
X represents $R_8$, $OR_8$, $NR_8R_9$,

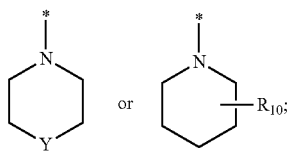

$R_8$ is $(C_{5-7})$cycloalkyl optionally comprising a heteroatom selected from O, S, SO and $SO_2$;
$R_9$ is H or $(C_{1-4})$alkyl;
$R_{10}$ represents 1-3 substituents independently selected from H, $(C_{1-3})$alkyl, halogen, oxo, CN and $CF_3$;
Y is $CF_2$, O, S, SO or $SO_2$;
or a pharmaceutically acceptable salt thereof, as agonists of the cannabinoid CB2 receptor, which can be used in the treatment of pain such as for example peri-operative pain, chronic pain, neuropathic pain, cancer pain and pain and spasticity associated with multiple sclerosis.

BRIEF DESCRIPTION OF THE FIGURE

FIG. 1. The effect of acute oral administration of compound 12 on neuropathy-induced mechanical allodynia in rats.

The reading at 0 min denotes the post-surgery withdrawal threshold (the difference between the pre-surgery and 0 min reading denotes the development of mechanical allodynia), this reading was followed by administration of test compound. Data are expressed as mean±s.e.m.

DESCRIPTION OF THE INVENTION

The term $(C_{1-6})$alkyl as used in the definition of Formula I means a branched or unbranched alkyl group having 1-6 carbon atoms, like hexyl, pentyl, butyl, isobutyl, tertiary butyl, propyl, isopropyl, ethyl and methyl.

The term $(C_{1-4})$alkyl likewise means a branched or unbranched alkyl group having 1-4 carbon atoms, like n-butyl, tert-butyl, propyl, isopropyl, ethyl and methyl.

The term $(C_{1-3})$alkyl likewise means a branched or unbranched alkyl group having 1-3 carbon atoms, like propyl, isopropyl, ethyl and methyl.

The meaning of the $(C_{1-3})$alkyl in the terms $(C_{1-3})$alkyloxy and $(C_{1-3})$alkyloxycarbonyl is as defined above.

The term $(C_{3-6})$cycloalkyl means a cycloalkyl group having 3-6 carbon atoms, like cyclohexyl, cyclopentyl, cyclobutyl and cyclopropyl.

The term $(C_{3-5})$cycloalkyl means a cycloalkyl group having 3-5 carbon atoms, like cyclopentyl, cyclobutyl and cyclopropyl.

The term $(C_{5-7})$cycloalkyl likewise means a cycloalkyl group having 5-7 carbon atoms. The preferred $(C_{5-7})$cycloalkyl is cyclohexyl.

The term halogen means F, Cl, Br or I.

There is a preference for 1-(4-(pyridin-2-yl)benzyl)imidazolidine-2,4-dione derivatives according to Formula I, wherein $R_2$, $R_3$ and $R_5$ are H. Also preferred are the compounds according to Formula I wherein $R_1$ is $(C_{1-4})$alkyl. Further preferred are the compounds according to Formula I wherein X represents $NR_8R_9$,

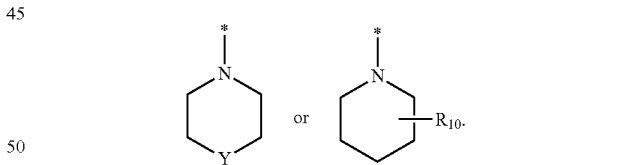

More preferred are the compounds of formula I wherein X is $NR_8R_9$ and $R_8$ is cyclohexyl optionally comprising a heteroatom selected from O and S.

Further preferred are compounds wherein $R_4$ is a F substituent at the position ortho to the $CR_6R_7X$ group.

Specifically preferred 1-(4-(pyridin-2-yl)benzyl)imidazolidine-2,4-dione derivatives of the invention are:
3-Isobutyl-1-(4-(6-(piperidin-1-ylmethyl)pyridin-2-yl)benzyl)imidazolidine-2,4-dione;
3-isobutyl-1-(4-(6-(morpholinomethyl)pyridin-2-yl)benzyl)imidazolidine-2,4-dione;
1-(4-(5-Fluoro-6-(((tetrahydro-2H-pyran-4-ylamino)methyl)pyridin-2-yl)benzyl)-3-isobutylimidazolidine-2,4-dione;
1-(4-(6-(((1,1-Dioxo-1λ$^6$-thiomorpholin-4-yl)methyl)pyridin-2-yl)benzyl)-3-isobutylimidazolidine-2,4-dione;

1-(4-(6-(((1,1-Dioxo-1λ⁶-thiomorpholin-4-yl)methyl)-5-fluoropyridin-2-yl)benzyl)-3-isobutylimidazolidine-2,4-dione;
3-Isobutyl-1-(4-(6-(((tetrahydro-2H-pyran-4-ylamino)methyl)pyridin-2-yl)benzyl)imidazolidine-2,4-dione;
3-Ethyl-1-(4-(6-(piperidin-1-ylmethyl)pyridin-2-yl)benzyl)imidazolidine-2,4-dione;
3-Ethyl-1-(4-(5-fluoro-6-(piperidin-1-ylmethyl)pyridin-2-yl)benzyl)imidazolidine-2,4-dione;
1-(4-(6-(1,1-Dioxo-1λ⁶-thiomorpholin-4-ylmethyl)-5-fluoropyridin-2-yl)benzyl)-3-ethylimidazolidine-2,4-dione;
1-(4-(6-(1,1-dioxo-1λ⁶-thiomorpholin-4-ylmethyl)pyridin-2-yl)benzyl)-3-ethylimidazolidine-2,4-dione;
1-(4-(5-Fluoro-6-(((tetrahydro-2H-pyran-4-ylamino)methyl)pyridin-2-yl)benzyl)-3-propylimidazolidine-2,4-dione;
1-(4-(6-(1,1-Dioxo-1λ⁶-thiomorpholin-4-ylmethyl)-5-fluoropyridin-2-yl)benzyl)-3-propylimidazolidine-2,4-dione;
3-(2,2-Difluoroethyl)-1-(4-(6-(piperidin-1-ylmethyl)pyridin-2-yl)benzyl)imidazolidine-2,4-dione;
3-(2,2-Difluoroethyl)-1-(4-(5-fluoro-6-(piperidin-1-ylmethyl)pyridin-2-yl)benzyl)imidazolidine-2,4-dione;
3-(Cyclopropylmethyl)-1-(4-(5-fluoro-6-(piperidin-1-ylmethyl)pyridin-2-yl)benzyl)imidazolidine-2,4-dione;
3-(Cyclopropylmethyl)-1-(4-(6-(piperidin-1-ylmethyl)pyridin-2-yl)benzyl)imidazolidine-2,4-dione;
3-(2-Oxopropyl)-1-(4-(6-(piperidin-1-ylmethyl)pyridin-2-yl)benzyl)imidazolidine-2,4-dione;
1-(4-(5-Fluoro-6-(piperidin-1-ylmethyl)pyridin-2-yl)benzyl)-3-(2-oxopropyl)imidazolidine-2,4-dione;
1-(4-(6-(1,1-Dioxo-1λ⁶-thiomorpholin-4-ylmethyl)-5-fluoropyridin-2-yl)benzyl)-3-(2-oxopropyl)imidazolidine-2,4-dione;
3-Isopropyl-1-(4-(6-(piperidin-1-ylmethyl)pyridin-2-yl)benzyl)imidazolidine-2,4-dione;
1-(4-(6-(1,1-Dioxo-1λ⁶-thiomorpholin-4-ylmethyl)-5-fluoropyridin-2-yl)benzyl)-3-isopropylimidazolidine-2,4-dione;
1-(4-(6-(1,1-Dioxo-1λ⁶-thiomorpholin-4-ylmethyl)pyridin-2-yl)benzyl)-3-isopropylimidazolidine-2,4-dione;
3-Cyclopropyl-1-(4-(5-fluoro-6-(piperidin-1-ylmethyl)pyridin-2-yl)benzyl)imidazolidine-2,4-dione;
3-Cyclopropyl-1-(4-(6-(1,1-dioxo-1λ⁶-thiomorpholin-4-ylmethyl)-5-fluoropyridin-2-yl)benzyl)imidazolidine-2,4-dione;
3-Cyclobutyl-1-(4-(5-fluoro-6-(((tetrahydro-2H-pyran-4-ylamino)methyl)pyridin-2-yl)benzyl)imidazolidine-2,4-dione;
3-Cyclobutyl-1-(4-(6-(((tetrahydro-2H-pyran-4-ylamino)methyl)pyridin-2-yl)benzyl)imidazolidine-2,4-dione;
3-Cyclobutyl-1-(4-(6-(1,1-dioxo-1λ⁶-thiomorpholin-4-ylmethyl)-5-fluoropyridin-2-yl)benzyl)imidazolidine-2,4-dione;
3-Cyclobutyl-1-(4-(6-(1,1-dioxo-1λ⁶-thiomorpholin-4-ylmethyl)pyridin-2-yl)benzyl)imidazolidine-2,4-dione;
1-(4-(6-(Piperidin-1-ylmethyl)pyridin-2-yl)benzyl)-3-(2,2,2-trifluoroethyl)imidazolidine-2,4-dione;
1-(4-(6-(1,1-Dioxo-1λ⁶-thiomorpholin-4-ylmethyl)-5-fluoropyridin-2-yl)benzyl-3-(2,2,2-trifluoroethyl)imidazolidine-2,4-dione;
1-(4-(6-((Tetrahydro-2H-pyran-4-ylamino)methyl)pyridin-2-yl)benzyl)-3-(2,2,2-trifluoro-ethyl)imidazolidine-2,4-dione;
1-(4-(5-Fluoro-6-(((tetrahydro-2H-pyran-4-ylamino)methyl)pyridin-2-yl)benzyl)-3-(2,2,2-trifluoroethyl)imidazolidine-2,4-dione; or a pharmaceutically acceptable salt thereof.

The 1-(4-(pyridin-2-yl)benzyl)imidazolidine-2,4-dione derivatives of the invention having Formula I can be prepared by methods known in the art of organic chemistry.

Compounds of the invention can for example be obtained from a Suzuki coupling reaction using potassium carbonate and a palladium (0) complex such as Pd(Ph₃P)₄ between a 2-bromopyridine derivative of Formula II, wherein $R_4$, $R_6$, $R_7$ and X have the meaning as previously defined, with a boronic acid derivative of Formula IV which is prepared from a benzylated imidazolidine of Formula III, wherein $R_1$, $R_2$, $R_3$ and $R_5$ have the meaning as previously defined (see Scheme I). Compounds of Formula II, wherein X represents $R_8$ and $R_8$ is $(C_{5-7})$cycloalkyl comprising a heteroatom selected from S and O, can be prepared (see Scheme II) from the condensation of a pyridine dibromide derivative of formula 1, wherein $R_4$ has the meaning as previously defined, with a nitrile derivative of formula 2, wherein Z is

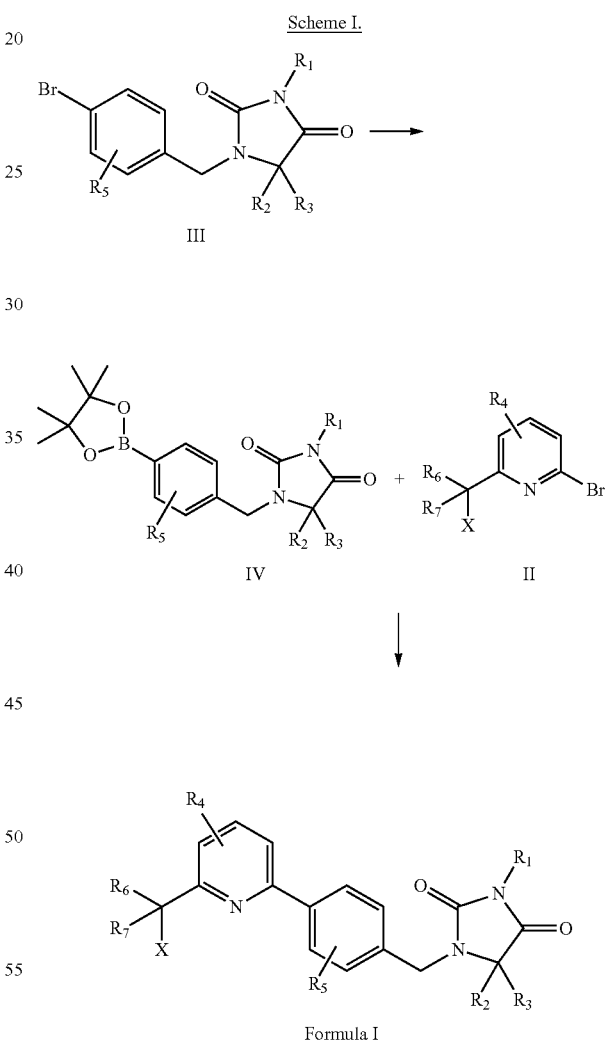

CH₂, O or S, to give the intermediate keto-derivative of formula 3, which can either be reduced via the hydrazide derivative of formula 4 to produce the compound of formula IIb, corresponding to a compound of formula II wherein $R_6$ and $R_7$ are H, or which can be reduced with the aid of diethylaminosulfur trifluoride to give a compound of formula IIa, corresponding to a compound of formula II wherein $R_6$ and $R_7$ are F.

Scheme II.

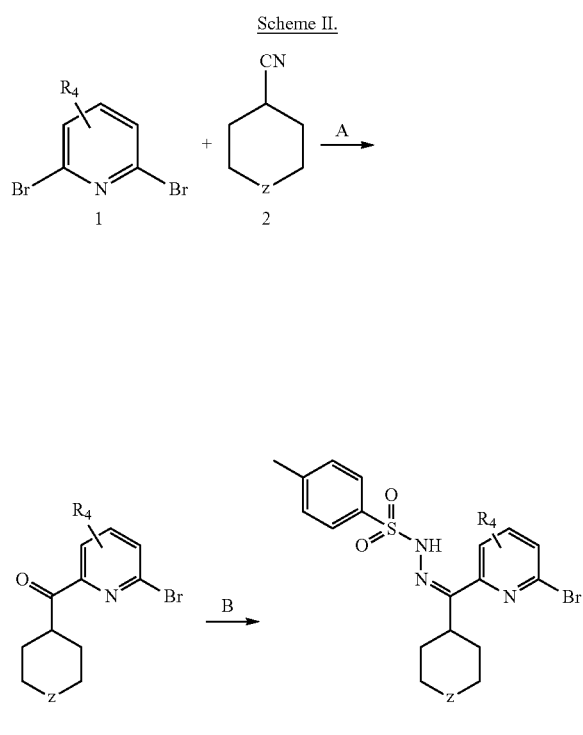

Scheme III.

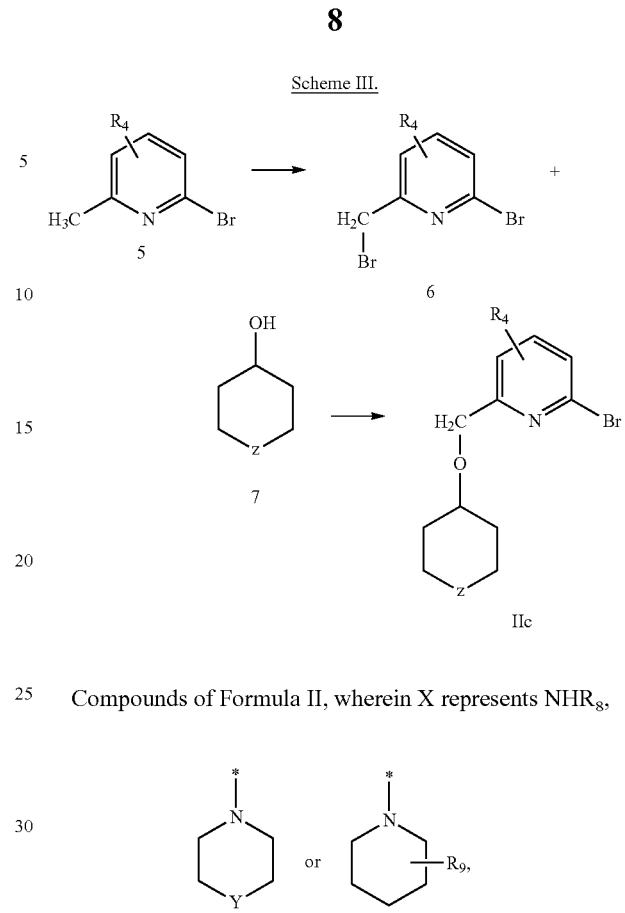

Compounds of Formula II, wherein X represents $NHR_8$,

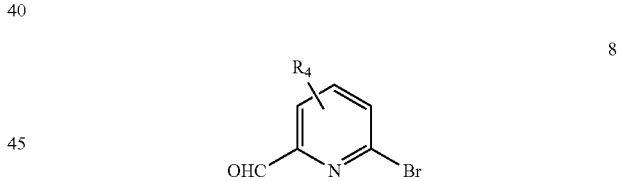

can be prepared using a reductive amination reaction, for instance with the use of acetic acid/sodium triacetoxyborohydride, of a carbaldehyde derivative of formula 8 with an appropriate amine derivative of formula X-H.

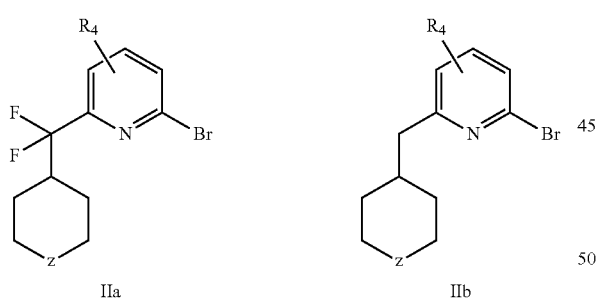

Conditions:

A: butyllithium/$H_2SO_4$  B: 4-methylbenzenesulfonyl hydrazide  C: diisobutylaluminum hydride  D: diethylaminosulfur trifluoride Compounds of Formula II, wherein X represents $OR_8$ can be prepared as depicted in Scheme III starting with bromination of a 2-bromo-6-methylpyridine derivative of formula 5 with the aid of N-bromosuccinimide/azo-di-isobutyronitrile to give the corresponding 6-bromomethyl derivative of formula 6 which is reacted with an alcohol derivative of formula 7, wherein Z is $CH_2$, O or S, to give a compound of formula IIc.

Compounds of formula III can be prepared by coupling of the amino acid $H_2N—C(R_2,R_3)—COOH$ with a 4-bromobenzaldehyde derivative of formula 9 under reductive amination conditions to obtain the N-benzyl derivative of formula 12, which is subsequently coupled with the amine $H_2N—R_1$, wherein $R_1$ has the previously defined meaning, with the aid of an amide bond forming reagent, such as dicyclohexylcarbodiimide (DCCI), TBTU or PyBOP or the like, to the amide derivative 13 from which the imidazolidine-2,4-dione derivative of formula III can be prepared by a ring closure reaction using carbonyldiimidazole.

In an alternative route which is denoted in Scheme IV the 4-bromobenzaldehyde derivative of formula 9 is coupled to the amino acid amide of formula $H_2N—C(R_2,R_3)—CONH_2$ under reductive amination conditions to obtain the N-benzyl derivative of formula 10, which can be converted to a compound of formula III by cyclisation using carbonyldiimidazole and subsequent alkylation with a halogenide of formula $Hal-R_1$.

Scheme IV.

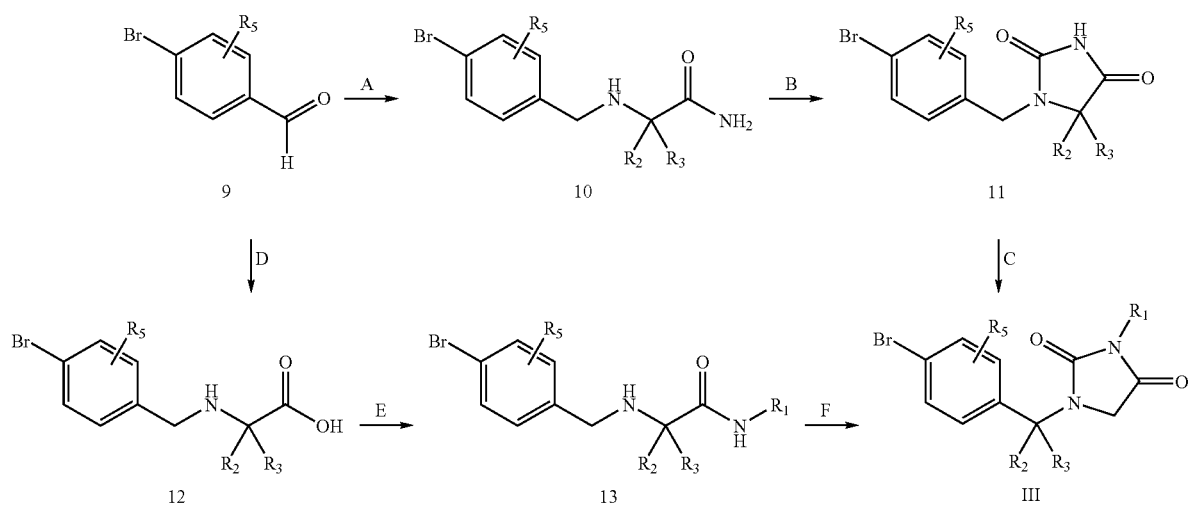

Conditions:

A: glycinamide hydrochloride/NaOH/NaBH$_4$. B: CDI/DMAP. C: R$_1$-halide/potassium carbonate D: glycine hydrochloride/NaOH/NaBH$_4$ E:R$_1$-amine/o-(7-azabenzotriazol-1-yl)-1,1,3,3-tetramethyluronium hexafluorophosphate. F: CDI/DMAP. G: bis(pinacolato)diboron/potassium acetate/1,1'-bis(diphenylphosphino)ferrocenedichloro palladium(II)

The 1-(4-(pyridin-2-yl)benzyl)imidazolidine-2,4-dione derivatives of Formula I and their salts may contain at least one centre of chirality, and exist therefore as stereoisomers, including enantiomers and diastereomers. The present invention includes the aforementioned stereoisomers within its scope and each of the individual R and S enantiomers of the compounds of Formula I and their salts, substantially free base, i.e. associated with less than 5%, preferably less than 2%, in particular less than 1% of the other enantiomer, and mixtures of such enantiomers in any proportions including the racemic mixtures containing substantially equal amounts of the two enantiomers.

Methods for asymmetric synthesis or chiral separation whereby the pure stereo-isomers are obtained are well known in the art, e.g. synthesis with chiral induction or starting from commercially available chiral substrates, or separation of stereo-isomers, for example using chromatography on chiral media or by crystallisation with a chiral counter-ion.

Pharmaceutically acceptable salts may be obtained by treating a free base of a 1-(4-(pyridin-2-yl)benzyl)imidazolidine-2,4-dione derivative of Formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid and methane sulfonic acid.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a 1-(4-(pyridin-2-yl)benzyl)imidazolidine-2,4-dione derivative according to general Formula I, or a pharmaceutically acceptable salt thereof, in admixture with one or more pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, ocular or rectal administration, and the like, all in unit dosage forms for administration. A preferred route of administration is the oral route.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al, Remington: *The Science and Practice of Pharmacy* (20th Edition, Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol. The invention further includes a pharmaceutical composition, as described before, in combination with packaging material suitable for said composition, said packaging material including instructions for the use of the composition for the use as described before.

The 1-(4-(pyridin-2-yl)benzyl)imidazolidine-2,4-dione derivatives of the invention were found to be selective agonists of the CB2 receptor as compared to the CB1 receptor, as determined in a human CB2 and CB1 reporter assays using CHO cells. Methods to determine receptor binding as well as in vitro biological activity of cannabinoid receptor modulators are well known in the art. In general, expressed receptor is incubated with the compound to be tested and binding or stimulation or inhibition of a functional response is measured.

To measure a functional response isolated DNA encoding the CB2 or CB1 receptor gene, preferably the human receptor, is expressed in suitable host cells. Such a cell might be the Chinese Hamster Ovary cell, but other cells are also suitable. Preferably the cells are of mammalian origin.

Methods to construct recombinant CB2 or CB1 expressing cell lines are well known in the art (Sambrook et al, Molecular Cloning: a Laboratory Manual, Cold Spring Harbor Laboratory Press, Cold Spring Harbor, latest edition). Expression of the receptor is attained by expression of the DNA encoding the desired protein. Techniques for ligation of additional sequences and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then incubated with the test compound to observe binding, or stimulation or inhibition of a functional response.

Alternatively isolated cell membranes containing the expressed CB2 or the CB1 receptor may be used to measure binding of compound.

For measurement of binding radioactively or fluorescently labelled compounds may be used. The most widely used radiolabelled cannabinoid probe is ($^3$H)CP55940, which has approximately equal affinity for CB1 and CB2 binding sites.

Functional CB2 or CB1 agonist activity may be measured by determining the second messenger response, such as for example measurement of receptor mediated changes in cAMP or MAP kinase pathways. Thus, such a method involves expression of the CB2 or CB1 receptor on the cell surface of a host cell and exposing the cell to the test compound. The second messenger response is then measured. The level of second messenger will be reduced or increased, depending on the effect of the test compound upon binding to the receptor.

In addition to direct measurement of e.g. cAMP levels in the exposed cell, cells can be used which in addition to transfection with receptor encoding DNA are also transfected with a second DNA encoding a reporter gene, the expression of which correlates with receptor activation. In general, reporter gene expression might be controlled by any response element reacting to changing levels of second messenger. Suitable reporter genes are e.g. LacZ, alkaline phosphatase, firefly luciferase and green fluorescence protein. The principles of such transactivation assays are well known in the art and are described e.g. in Stratowa, C., Himmler, A. and Czernilofsky, A. P., *Curr. Opin. Biotechnol.* 6, 574 (1995). For selecting selective, active agonist compounds on the CB2 receptor the $EC_{50}$ value for a compound is $<10^{-5}$ M, preferably $<10^{-7}$ M and the selectivity over CB1 receptor agonist as defined as EC50 (CB1)/EC50 (CB2) is >10, preferably >50.

The compounds may be used as analgesic agents in the treatment of pain such as for example acute pain such as peri-operative pain, chronic pain, neuropathic pain, cancer pain, visceral pain, headache and spasticity associated with multiple sclerosis.

Cannabinoid agonists of the invention would also potentially be useful in the treatment of other disorders including, (intestinal) inflammation, atopic dermatitis, liver diseases, respiratory disorders, allergies, oncology, epilepsy, migraine, osteoporosis, cardiovascular disorders, acute neurodegenerative disorders, such as traumatic brain injury and stroke and slowly neurodegenerative disorders, such as Alzheimer's disease, multiple sclerosis and ALS (Parcher P, Batkai S, Kunos, G, The endocannabinoid system as an emerging target of pharmacotherapy, *Pharmacol Rev.* 2006, 58(3):389-462).

The compounds could also be used in conjunction with other drugs, for example analgesic drugs such as opioids and non-steroidal anti-inflammatory drugs (NSAIDs), including COX-2 selective inhibitors.

The compounds of the invention may be administered to humans in a sufficient amount and for a sufficient amount of time to alleviate the symptoms. Illustratively, dosage levels for humans can be in the range of 0.001-50 mg per kg body weight, preferably in a dosage of 0.01-20 mg per kg body weight.

The invention is illustrated by the following Examples.

Abbreviations: Boc: tert-butoxycarbonyl; $CDCl_3$: chloroform-d; DBU: 1,8-diazabicyclo(5.4.0)undec-7-ene; CDI: N,N'-carbonyldiimidazole; DCCI: 1,3-dicyclohexylcarbodiimide; DCM: dichloromethane; DIPEA: N,N-diisopropylethylamine; DMAP: 4-dimethylaminopyridine; DMF: N,N-dimethylformamide; $Et_3N$ or TEA: triethyl amine; Gly: glycinyl; HPLC: high performance liquid chromatography; HOAc: acetic acid; HOBt: 1-hydroxybenzo-triazole; MeOH: methanol; $Me_3SiCl$ or TMSCI: chlorotrimethylsilane; MS: mass spectrum; $(PPh_3)_4Pd$: tetrakis(triphenylphosphine)palladium(0); PyBOP: (benzotriazol-1-yloxy)tripyrrolidinophosphonium hexafluorophosphate; PyBrOP: bromo(tris pyrrolidino)phosphonium tetrafluorohosphate; TBTU: ((benzotriazol-1-yloxy)-dimethylamino-methylene)-dimethyl-ammonium tetrafluoro borate; TFA: trifluoroacetic acid; THF: tetrahydrofuran; TLC: thin layer chromatography.

Compound names were generated with Cambridgesoft's Chemdraw Ultra, version 9.0.7.

EXAMPLE 1

1-(4-bromobenzyl)-3-isobutylimidazolidine-2,4-dione

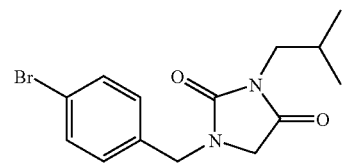

i) To a solution of 4-bromobenzaldehyde (100 g, 0.54 mol) and glycinamide hydrochloride (54 g, 0.48 mol) methanol/water (1500 ml, 5.5/1) was added sodium hydroxide (21.6 g, 0.54 mol). After stirring for 17 h at room temperature the reaction mixture was cooled to 0° C. Sodium borohydride (38 g, 1.0 mol) was added and the mixture was stirred until a clear solution was obtained. The reaction was quenched by addition of concentrated hydrochloric acid until pH=3. After stirring for 17 h the mixture was neutralized with a saturated aqueous solution of sodium hydrogen carbonate and the product was extracted into dichloromethane. The combined organic phases were washed with water, brine, dried over sodium sulfate and concentrated under reduced pressure to afford 2-(4-bromobenzylamino)acetamide (92 g).

ii) To a solution of the product obtained in the previous step (60.6 g, 0.25 mol) in acetonitrile (1500 ml) were added CDI (81 g, 0.5 mol) DMAP (61 g, 0.5 mol). After stirring for 16 h at 60° C. the solution was cooled to room temperature and poured into an aqueous solution of 2M hydrochloric acid. The product was extracted into ethyl acetate and the combined organic phases were washed with water, brine, dried over sodium sulfate and concentrated under reduced pressure. The remaining solid was stirred with acetone. Filtration afforded 1-(4-bromobenzyl)imidazolidine-2,4-dione (45 g) as a white solid. The product was used in the following step without further purification.

iii) To a solution of the product obtained in the previous step (10 g, 37.2 mmol) in DMF (90 ml) were added at room temperature, potassium carbonate (15.4 g, 111 mmol) and 1-bromo-2-methylpropane (8.08 ml, 74.3 mmol). After 17 h stirring at 50° C. under a nitrogen atmosphere the reaction mixture was cooled to room temperature and filtered. The clear solution was concentrated under reduced pressure. Column chromatography afforded 1-(4-bromobenzyl)-3-isobutylimidazolidine-2,4-dione (10.9 g) as a white solid.

EXAMPLE 2

Following a procedure analogous to that described in Example 1, the following compounds were prepared.

2A: 1-(4-Bromobenzyl)-3-methylimidazolidine-2,4-dione

1H NMR (400 MHz, CDCl3): δ 7.50 (d, J=8.61 Hz, 2H), 7.14 (d, J=8.61 Hz, 2H), 4.52 (s, 2H), 3.73 (s, 2H), 3.06 (s, 3H).

2B: 1-(4-Bromobenzyl)-3-ethylimidazolidine-2,4-dione

1H NMR (400 MHz, CDCl3): δ 7.50 (d, J=8.22 Hz, 2H), 7.13 (d, J=8.22 Hz, 2H), 4.52 (s, 2H), 3.71 (s, 2H), 3.59 (q, J=7.43 Hz, 2H), 1.24 (t, J=7.43 Hz, 3H).

2C: 1-(4-Bromobenzyl)-3-propylimidazolidine-2,4-dione

1H NMR (400 MHz, CDCl3): δ 7.49 (d, J=8.22 Hz, 2H), 7.13 (d, J=8.22 Hz, 2H), 4.51 (s, 2H), 3.72 (s, 2H), 3.50 (dd J=7.43 and 6.26 Hz, 2H), 1.72-1.60 (m, 2H), 0.93 (t, J=7.43 Hz, 3H).

2D: 1-(4-Bromobenzyl)-3-(2,2-difluoroethyl)imidazolidine-2,4-dione

1H NMR (400 MHz, CDCl3): δ 7.51 (d, J=8.22 Hz, 2H), 7.14 (d, J=8.22 Hz, 2H), 6.21-5.87 (tt, J=55.95, 4.70 and 4.30 Hz, 1H), 4.53 (s, 2H), 3.90 (td, J=13.70 and 4.30 Hz, 2H), 3.80 (s, 2H).

2E: 1-(4-Bromobenzyl)-3-(cyclopropylmethyl)imidazolidine-2,4-dione

1H NMR (400 MHz, CDCl3): δ 7.50 (d, J=8.22 Hz, 2H), 7.15 (d, J=8.22 Hz, 2H), 4.53 (s, 2H), 3.74 (s, 2H), 3.56 (d, J=7.44 Hz, 2H), 1.23-1.12 (m, 1H), 0.54-0.45 (m, 2H), 0.38-0.32 (m, 2H).

2F: 1-(4-Bromobenzyl)-3-(cyclobutylmethyl)imidazolidine-2,4-dione

1H NMR (400 MHz, CDCl3): δ 7.49 (d, J=8.22 Hz, 2H), 7.13 (d, J=8.22 Hz, 2H), 4.50 (s, 2H), 3.71 (s, 2H), 3.57 (d, J=7.43 Hz, 2H), 2.75-2.62 (m, 1H), 2.08-1.97 (m, 2H), 1.92-1.70 (m, 4H).

2G: 1-(4-Bromo-benzyl)-3-(2-methoxyethyl)imidazolidine-2,4-dione

1H NMR (400 MHz, CDCl3): δ 7.49 (d, J=8.22 Hz, 2H), 7.14 (d, J=8.22 Hz, 2H), 4.52 (s, 2H), 3.77-3.72 (m, 4H), 3.60 (t, J=5.87 Hz, 2H), 3.36 (s, 3H).

2H: methyl 2-(3-(4-bromobenzyl)-2,5-dioxoimidazolidin-1-yl)acetate

1H NMR (400 MHz, CDCl3): δ 7.50 (d, J=8.22 Hz, 2H), 7.15 (d, J=8.22 Hz, 2H), 4.55 (s, 2H), 4.30 (s, 2H), 3.83 (s, 2H), 3.78 (s, 3H).

2L: 1-(4-Bromo-benzyl)-3-(2-oxopropyl)imidazolidine-2,4-dione

1H NMR (400 MHz, CDCl3): δ 7.51 (d, J=8.61 Hz, 2H), 7.15 (d, J=8.61 Hz, 2H), 4.54 (s, 2H), 4.35 (s, 2H), 3.83 (s, 2H), 2.25 (s, 3H).

EXAMPLE 3

1-(4-Bromobenzyl)-3-isopropylimidazolidine-2,4-dione

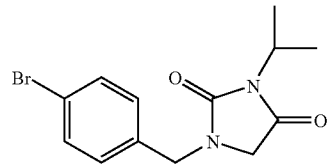

i) To a solution of glycine (8.11 g, 108 mmol) in water (40 ml) were added an aqueous solution of sodium hydroxide (108 mmol, 15 ml) and a solution of 4-bromobenzaldehyde (20 g, 108 mmol) in methanol (240 ml). After 30 minutes stirring at room temperature sodium borohydride (4.09 g, 108 mmol) was added portionwise to this suspension. After 18 h stirring at room temperature the reaction mixture was concentrated under reduced pressure and the resulting aqueous phase was washed with diethyl ether. The aqueous phase was neutralized by the addition of an aqueous solution of 2M hydrochloric acid. The resulting precipitate was collected by filtration, washed with water and diethyl ether. Drying the white solid afforded 2-(4-bromobenzylamino)acetic acid (14.2 g). The product was used in the following step without further purification.

ii) To a suspension of the product obtained in the previous step (1.7 g, 6.96 mmol) in dichloromethane (20 ml) were added triethylamine (1.94 ml, 13.9 mmol), isopropylamine (0.65 ml, 7.66 mmol) and o-(7-azabenzotriazol-1-yl)-1,1,3,3-tetramethyluronium hexafluorophosphate (3.18 g, 8.36 mmol). After 17 h stirring at room temperature the reaction mixture was concentrated under reduced pressure. Column chromatography afforded 2-(4-bromobenzylamino)-N-isopropylacetamide (1.95 g).

iii) To a solution of the product obtained in the previous step (1.95 g, 6.96 mmol) in acetonitrile were added (diimidazol-1-yl)ketone (2.26 g, 13.9 mmol) and 4-dimethylaminopyridine (1.70 g, 13.9 mmol). After 17 h stirring at 60° C., the reaction mixture was cooled to room temperature and quenched by addition of a saturated aqueous solution of sodium hydrogen carbonate. The product was extracted into ethylacetate and the combined organic phases were washed with water, brine and dried over sodium sulfate. Column chromatography afforded the title compound 1-(4-bromobenzyl)-3-isopropylimidazolidine-2,4-dione (1.8 g) as a light yellow oil.

1H NMR (400 MHz, CDCl3): δ 7.50 (d, J=8.61 Hz, 2H), 7.13 (d, J=8.61 Hz, 2H), 4.49 (s, 2H), 4.38-4.30 (m, 1H), 1.43 (d, J=6.65 Hz, 6H).

EXAMPLE 4

Following a procedure analogous to that described in Example 3, the following compounds were prepared.

4A: 1-(4-Bromobenzyl)-3-cyclopropylimidazolidine-2,4-dione

1H NMR (400 MHz, CDCl3): δ 7.50 (d, J=8.61 Hz, 2H), 7.14 (d, J=8.61 Hz, 2H), 4.48 (s, 2H), 3.66 (s, 2H), 2.65-2.56 (m, 1H), 0.97 (d, J=5.87 Hz, 4H).

4B: 1-(4-Bromobenzyl)-3-cyclobutylimidazolidine-2,4-dione

1H NMR (400 MHz, CDCl3): δ 7.49 (d, J=8.22 Hz, 2H), 7.14 (d, J=8.22 Hz, 2H), 4.60-4.51 (m, 1H), 4.49 (s, 2H), 3.65 (s, 2H), 2.95-2.82 (m, 2H), 2.23-2.13 (m, 2H), 1.91-1.81 (m, 1H), 1.79-1.65 (m, 1H).

4C: 1-(4-Bromobenzyl)-3-(2,2,2-trifluoroethyl)imidazolidine-2,4-dione

1H NMR (400 MHz, CDCl3): δ 7.52 (d, J=8.61 Hz, 2H), 7.15 (d, J=8.61 Hz, 2H), 4.55 (s, 2H), 4.16 (q, J=8.61 Hz, 2H), 3.83 (s, 2H).

4D: 1-(4-Bromobenzyl)-3-(1-cyclopropylethyl)imidazolidine-2,4-dione

1H NMR (400 MHz, CDCl3): δ 7.54 (d, J=8.61 Hz, 2H), 7.20 (d, J=8.61 Hz, 2H), 4.72 (s, 2H), 3.87 (s, 2H), 3.46-3.36 (m, 1H), 1.22 (d, J=6.65 Hz, 3H), 0.85-0.79 (m, 1H), 0.59-0.43 (m, 2H), 0.38-0.21 (m, 2H).

4E: (S)-1-(4-bromobenzyl)-3-(1-methoxypropan-2-yl)imidazolidine-2,4-dione

1H NMR (400 MHz, CDCl3): δ 7.49 (d, J=8.61 Hz, 2H), 7.13 (d, J=8.61 Hz, 2H), 4.50 (d, J=3.91 Hz, 2H), 4.46-4.39 (m, 1H), 3.69 (s, 2H), 3.34 (s, 3H), 1.18 (d, J=7.04 Hz, 3H).

4F: 1-(4-Bromobenzyl)-3-(tetrahydrofuran-3-yl)imidazolidine-2,4-dione

1H NMR (400 MHz, CDCl3): δ 7.50 (d, J=8.61 Hz, 2H), 7.14 (d, J=8.61 Hz, 2H), 4.78-4.69 (m, 1H), 4.50 (s, 2H), 4.19-4.11 (m, 1H), 4.03-3.84 (m, 3H), 3.70 (s, 2H), 2.41-2.32 (m, 1H), 2.26-2.14 (m, 1H).

4G: 1-(4-Bromobenzyl)-3-(oxazol-5-ylmethyl)imidazolidine-2,4-dione

1H NMR (400 MHz, CDCl3): δ 7.83 (s, 1H), 7.50 (d, J=8.61 Hz, 2H), 7.15-7.11 (m, 3H), 4.77 (s, 2H), 4.52 (s, 2H), 3.77 (s, 2H).

EXAMPLE 5

2-Bromo-6-(piperidin-1-ylmethyl)pyridine

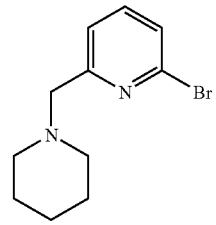

i) To a solution of 6-bromopyridine-2-carbaldehyde (25 g, 135 mmol) in dichloromethane (500 ml) was slowly added piperidine (12.6 g, 149 mmol) at 10° C. After stirring for 15 minutes at 10° C., acetic acid (8.9 g, 149 mmol) was added, followed by the portionwise addition of sodium triacetoxyborohydride, while the temperature was kept at 5-10° C. After stirring for 2 h at room temperature the reaction mixture was poured into a saturated aqueous solution of sodium hydrogen carbonate. The product was extracted into dichloromethane and the combined organic phases were washed with brine, dried over sodium sulphate and concentrated under reduced pressure. Column chromatography afforded 2-bromo-6-(piperidin-1-ylmethyl)pyridine (30 g) as a colourless oil.

1H NMR (400 MHz, CDCl3): δ 7.54-7.43 (m, 2H), 7.33 (d, J=7.43 Hz, 1H), 3.60 (s, 2H), 2.48-2.38 (m, 4H), 1.63-1.54 (m, 4H), 1.48-1.39 (m, 2H).

EXAMPLE 6

Following a procedure analogous to that described in Example 5, the following compounds were prepared.

6A: 4-((6-Bromopyridin-2-yl)methyl)thiomorpholine 1,1-dioxide

1H NMR (400 MHz, CDCl3): δ 7.61-7.54 (dd, J=7.83 and 7.43 Hz, 1H), 7.42 (d, J=7.83 Hz, 1H), 7.39 (d, J=7.43 Hz, 1H), 3.81 (s, 2H), 3.14-3.04 (m, 8H).

6B: 4-((6-Bromopyridin-2-yl)methyl)morpholine

1H NMR (400 MHz, CDCl3): δ 7.53 (dd, J=7.83 and 7.43 Hz, 1H), 7.45 (d, J=7.83 Hz, 1H), 7.37 (d, J=7.43 Hz, 1H), 3.76-3.71 (m, 4H), 3.65 (s, 2H), 2.55-2.49 (m, 4H).

6C: 2-Bromo-6-((3-methylpiperidin-1-yl)methyl)pyridine

1H NMR (400 MHz, CDCl3): δ 7.47-7.37 (m, 2H), 7.26 (d, J=7.43 Hz, 1H), 3.54 (s, 2H), 2.76-2.64 (m, 2H), 1.92 (td, J=10.96 and 3.52 Hz, 1H), 1.68-1.44 (m, 5H), 0.87-0.72 (m, 4H).

6D: 2-Bromo-6-((3,3-difluoropiperidin-1-yl)methyl)pyridine

1H NMR (400 MHz, CDCl3): δ 7.58-7.49 (m, 2H), 7.47 (d, J=7.43 Hz, 1H), 3.74 (s, 2H), 2.71 (dd, J=11.35 and 10.96 Hz, 2H), 2.54 (dd, J=5.48 and 5.09 Hz, 2H), 1.97-1.84 (m, 2H), 1.83-1.76 (m, 2H).

6E: 2-Bromo-6-((3-fluoropiperidin-1-yl)methyl)pyridine

1H NMR (400 MHz, CDCl3): δ 7.53 (dd, J=7.83 and 7.43 Hz, 1H), 7.47 (d, J=7.43 Hz, 1H), 7.36 (d, J=7.83 Hz, 1H), 4.76-4.56 (m, 1H), 3.68 (s, 2H), 2.82-2.71 (m, 1H), 2.60-2.47 (m, 2H), 2.43-2.36 (m, 1H), 1.93-1.78 (m, 2H), 1.73-1.50 (m, 2H).

6F: 2-Bromo-6-((3-trifluoromethylpiperidin-1-yl)methyl)pyridine (m/z)=324 (M+H)+

6G: 1-((6-Bromopyridin-2-yl)methyl)-piperidin-3-one

1H NMR (400 MHz, CDCl3): δ 7.54 (dd, J=7.83 and 7.43 Hz, 1H), 7.41 (d, J=7.43 Hz, 1H), 7.38 (d, J=7.83 Hz, 1H), 3.73 (s, 2H), 3.08 (s, 2H), 2.73 (dd, J=5.48 Hz, 2H), 2.39 (dd, J=7.04 Hz, 2H), 2.03-1.94 (m, 2H).

6H: N-((6-bromopyridin-2-yl)methyl)tetrahydro-2H-pyran-4-amine

1H NMR (400 MHz, CDCl3): δ 7.52 (dd, J=7.83 and 7.43 Hz, 1H), 7.37 (d, J=7.83 Hz, 1H), 7.31 (d, J=7.43 Hz, 1H), 4.02-3.96 (m, 2H), 3.93 (s, 2H), 3.39 (td, J=11.74 and 2.35 Hz, 2H), 2.78-2.69 (m, 1H), 1.90-1.82 (m, 2H), 1.55-1.42 (m, 2H).

6I: ((6-Bromopyridin-2-yl)methyl)cyclohexylamine

1H NMR (400 MHz, CDCl3): δ 7.50 (dd, J=7.83 and 7.43 Hz, 1H), 7.34 (d, J=7.83 Hz, 1H), 7.31 (d, J=7.43 Hz, 1H), 3.90 (s, 2H), 2.50-2.41 (m, 1H), 1.96-1.88 (m, 2H), 1.78-1.69 (m, 3H), 1.65-1.57 (m, 1H), 1.31-1.06 (m, 5H).

6J: N-((6-bromopyridin-2-yl)methyl)tetrahydro-2H-pyran-3-amine

1H NMR (400 MHz, CDCl3): δ 7.51 (dd, J=7.83 and 7.43 Hz, 1H), 7.36 (d, J=7.83 Hz, 1H), 7.31 (d, J=7.43 Hz, 1H), 3.96-3.89 (m, 3H), 3.83 (m, 1H), 3.47-3.39 (m, 1H), 3.27-3.20 (dd, J=8.61 and 8.22 Hz, 1H), 2.71-2.63 (m, 1H), 2.04-1.96 (m, 1H), 1.76-1.43 (m, 3H), 1.48-1.37 (m, 1H).

6K: 4-((6-Bromopyridin-2-yl)methyl)thiomorpholine

1H NMR (400 MHz, CDCl3): δ 7.53 (dd, J=7.83 and 7.43 Hz, 1H), 7.42 (d, J=7.83 Hz, 1H), 7.37 (d, J=7.43 Hz, 1H), 3.67 (s, 2H), 2.84-2.66 (m, 8H).

EXAMPLE 7

Following a procedure analogous to that described in Example 5 using 6-bromo-3-fluoropyridine-2-carbaldehyde as the starting material, the following compounds were prepared.

7A: 4-((6-Bromo-3-fluoropyridin-2-yl)methyl)thiomorpholine 1,1-dioxide

1H NMR (400 MHz, CDCl3): δ 7.45 (dd, J=8.22 and 3.52 Hz, 1H), 7.32 (d, J=8.61 and 8.22 Hz, 1H), 3.89 (d, J=2.74 Hz, 2H), 3.17 (m, 8H).

7B: 4-((6-Bromo-3-fluoropyridin-2-yl)methyl)morpholine

1H NMR (400 MHz, CDCl3): δ 7.41 (dd, J=8.22 and 3.52 Hz, 1H), 7.28 (d, J=8.61 and 8.22 Hz, 1H), 3.73-3.69 (m, 6H), 2.61-2.54 (m, 4H).

7C: 6-Bromo-3-fluoro-2-((3-methylpiperidin-1-yl)methyl)pyridine (m/z)=288 (M+H)+

7D: 6-Bromo-3-fluoro-2-(piperidin-1-ylmethyl)pyridine

1H NMR (400 MHz, CDCl3): δ 7.38 (dd, J=8.22 and 3.52 Hz, 1H), 7.26 (d, J=8.61 and 8.22 Hz, 1H), 3.69 (d, J=2.74 Hz, 2H), 2.54-2.46 (m, 4H), 1.61-1.53 (m, 4H), 1.45-1.36 (m, 2H).

7E: 6-Bromo-2-((3,3-dimethylpiperidin-1-yl)methyl)-3-fluoropyridine

1H NMR (400 MHz, CDCl3): δ 7.37 (dd, J=8.22 and 3.52 Hz, 1H), 7.25 (d, J=8.61 and 8.22 Hz, 1H), 3.66 (d, J=2.35 Hz, 2H), 2.41 (bs, 2H), 2.10 (bs, 2H), 1.60-1.53 (m, 2H), 1.22-1.13 (m, 2H), 0.90 (s, 6H).

7F: 6-Bromo-2-((3,3-difluoropiperidin-1-yl)methyl)-3-fluoropyridine

1H NMR (400 MHz, CDCl3): δ 7.41 (dd, J=8.22 and 3.52 Hz, 1H), 7.29 (d, J=8.61 and 8.22 Hz, 1H), 3.86 (d, J=2.35 Hz, 2H), 2.79 (dd, J=11.35 and 10.95 Hz, 2H), 2.59 (dd, J=5.48 and 5.09 Hz, 2H), 1.91-1.72 (m, 4H).

7G: 6-Bromo-3-fluoro-2-((3-fluoropiperidin-1-yl)methyl)pyridine

1H NMR (400 MHz, CDCl3): δ 7.40 (dd, J=8.61 and 3.52 Hz, 1H), 7.28 (d, J=8.61 and 8.22 Hz, 1H), 4.72-4.53 (m, 1H), 3.78 (bs, 2H), 2.97-2.86 (m, 1H), 2.60-2.57 (m, 1H), 2.55-2.47 (m, 1H), 2.42-2.35 (m, 1H), 1.92-1.75 (m, 2H), 1.62-1.47 (m, 2H).

7H: 6-Bromo-3-fluoro-2-((3-trifluoromethylpiperidin-1-yl)methyl)pyridine (m/z)=342 (M+H)+

7I: N-((6-bromo-3-fluoropyridin-2-yl)methyl)tetrahydro-2H-pyran-4-amine

1H NMR (400 MHz, CDCl3): δ 7.37 (dd, J=8.61 and 3.52 Hz, 1H), 7.26 (d, J=8.61 and 8.22 Hz, 1H), 4.04-3.95 (m, 4H), 3.40 (td, J=11.73 and 1.96 Hz, 2H), 2.76-2.66 (m, 1H), 1.90-1.81 (m, 2H), 1.56-1.42 (m, 2H).

7J: N-((6-bromo-3-fluoropyridin-2-yl)methyl)cyclohexanamine

1H NMR (400 MHz, CDCl3): δ 7.35 (dd, J=8.61 and 3.52 Hz, 1H), 7.24 (d, J=8.61 and 8.22 Hz, 1H), 3.96 (d, J=2.35 Hz, 2H), 2.50-2.40 (m, 1H), 1.98-1.85 (m, 3H), 1.79-1.70 (m, 2H), 1.65-1.58 (m, 1H), 1.32-1.09 (m, 5H).

7K: 1-((6-bromo-3-fluoropyridin-2-yl)methyl)piperidine-3-carbonitrile

1H NMR (400 MHz, CDCl3): δ 7.41 (dd, J=8.61 and 3.52 Hz, 1H), 7.29 (d, J=8.61 and 8.22 Hz, 1H), 3.77 (d, J=2.35 Hz, 2H), 2.96-2.87 (m, 1H), 2.82-2.72 (m, 1H), 2.71-2.63 (m, 1H), 2.62-2.53 (m, 1H), 2.46-2.36 (m, 1H), 1.93-1.71 (m, 2H), 1.64-1.52 (m, 2H).

7L: 4-((6-Bromo-3-fluoropyridin-2-yl)methyl)thiomorpholine

1H NMR (400 MHz, CDCl3): δ 7.40 (dd, J=8.61 and 3.52 Hz, 1H), 7.32 (d, J=8.61 and 8.22 Hz, 1H), 3.75 (d, J=2.74 Hz, 2H), 2.87-2.81 (m, 4H), 2.71-2.65 (m, 4H).

EXAMPLE 8

Following a procedure analogous to that described in Example 5 using 2-bromo-pyridine-4-carbaldehyde as the starting material, the following compound was prepared.

2-bromo-4-(piperidin-1-ylmethyl)pyridine

1H NMR (400 MHz, CDCl3): δ 8.27 (d, J=5.09, 1H), 7.48 (s, 1H), 7.23 (d, J=5.09 Hz, 1H), 3.93 (s, 2H), 2.41-2.31 (m, 4H), 1.63-1.55 (m, 4H), 1.50-1.39 (m, 2H).

EXAMPLE 9

6-bromo-3-fluoro-2-((tetrahydro-2H-pyran-4-yloxy)methyl)pyridine

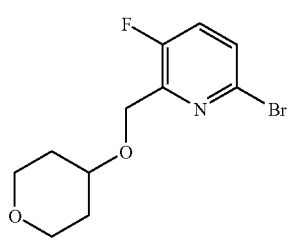

i) To a solution of 6-bromo-3-fluoro-2-methylpyridine (0.5 gr, 2.63 mmol) in dichloromethane (5 ml) were added at room temperature N-bromosuccinimide (937 mg, 5.26 mmol) and azo-di-isobutyronitrile (86 mg, 0.526 mmol). After 17 h stirring at 55° C. the reaction mixture was quenched by the addition of water and the product was extracted into dichloromethane. The combined organic phases were washed with brine, dried over sodium sulfate and concentrated under reduced pressure. Column chromatography afforded 6-bromo-2-(bromomethyl)-3-fluoropyridine (388 mg) as a clear oil.

ii) To a solution of the product obtained in the previous step (388 mg, 1.44 mmol) and tetrahydro-2H-pyran-4-ol (0.206 ml, 2.16 mmol) in tetrahydrofuran (10 ml) was added sodium hydride (69.3 mg, 2.31 mmol, 80% dispersion in oil). After 1 h stirring at room temperature the reaction mixture was quenched by the addition of water and the product was extracted into dichloromethane. The combined organic phases were washed with brine, dried over sodium sulfate and concentrated under reduced pressure. Column chromatography afforded the title compound 6-bromo-3-fluoro-2-((tetrahydro-2H-pyran-4-yloxy)methyl)pyridine (177 mg) as a clear oil.

1H NMR (400 MHz, CDCl3): δ 7.44 (dd, J=8.61 and 3.52 Hz, 1H), 7.31 (d, J=8.61 and 8.22 Hz, 1H), 4.67 (d, J=2.35 Hz, 2H), 3.99-3.92 (m, 2H), 3.72-3.64 (m, 1H), 3.49-3.41 (m, 2H), 2.00-1.91 (m, 2H), 1.71-1.60 (m, 2H).

EXAMPLE 10

2-Bromo-6-(cyclohexylmethyl)pyridine i) A solution of 2,6-dibromopyridine (1.37 g, 5.8 mmol) in THF/hexane/diethyl ether (1/1/3, 15 ml) was added dropwise, under a nitrogen atmosphere, to a solution of a 2.5 M n-butyllithium in hexane (2.43 ml, 6.08 mmol) at −78° C.

After 10 minutes stirring, a solution of cyclohexanecarbonitrile (633 mg, 5.8 mmol) in THF/hexane/diethyl ether (1/1/3, 4 ml) was added and the reaction mixture was stirred for 2.5 h at −78° C. The reaction mixture was warmed to room temperature and stirred for another 1.5 h. The reaction mixture was quenched by the addition of an aqueous solution of 2M sulfuric acid (7 ml). after vigorous stirring for 2 h, water was added and the product was extracted into diethyl ether. The combined organic phases were washed with a saturated aqueous solution of sodium hydrogen carbonate, brine, dried over sodium sulfate and concentrated under reduced pressure. Column chromatography afforded (6-bromo-pyridin-2-yl)(cyclohexyl)methanone (800 mg) as a clear oil.

ii) A suspension of the product obtained in the previous step (600 mg, 2.24 mmol) and 4-methylbenzenesulfonyl hydrazide (458 mg, 2.46 mmol) in ethanol (2 ml) was heated to 100° C. for 15 minutes, in a microwave. After cooling to room temperature the reaction mixture concentrated under reduced pressure. Column chromatography afforded N'-((6-bromopyridin-2-yl)(cyclohexyl)methylene)-4-methylbenzenesulfonohydrazide (608 mg) as a white solid.

iii) To a solution of the product obtained in the previous step (600 mg, 1.38 mmol) in 4 ml dichloromethane was added slowly to a solution of 20% diisobutylaluminiumhydride in toluene (0.97 g, 13.8 mmol). After 17 h stirring at room temperature the reaction mixture was quenched by adding slowly an aqueous solution of 2M sodium hydroxide until pH=10. The product was extracted into ethylacetate and the combined organic phases were washed with water, brine, dried over sodium sulfate and concentrated under reduced pressure. Column chromatography afforded the title compound 2-bromo-6-(cyclohexylmethyl)pyridine as a white solid.

1H NMR (400 MHz, CDCl3): δ 7.42-7.21 (m, 3H), 3.62 (d, J=7.04 Hz, 2H), 1.81-0.85 (m, 11H).

EXAMPLE 11

2-Bromo-6-(difluoro-(tetrahydro-2H-pyran-4-yl)methyl)pyridine

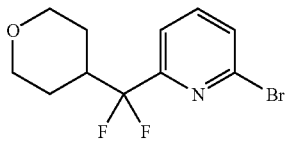

i) (6-Bromo-pyridin-2-yl)-(tetrahydro-2H-pyran-4-yl)methanone was prepared following a procedure analogous to that described in Example 10, step i), using tetrahydro-2H-pyran-4-carbonitrile as the starting material.

ii) To a solution of the product obtained in the previous step (200 mg, 0.74 mmol) in dichloromethane (2 ml) was added portionwise, over a period of 6 days, di-ethylaminosulfur-trifluoride (1.49 g, 9.25 mmol), under a nitrogen atmosphere. After completion the reaction mixture was quenched carefully by addition of methanol and the product was extracted into ethylacetate. The combined organic phases were washed with water, brine, dried over sodium sulfate and concentrated under reduced pressure. Column chromatography afforded the title compound 2-bromo-6-(difluoro-(tetrahydro-2H-pyran-4-yl)methyl)pyridine (144 mg) as a clear oil.

1H NMR (400 MHz, CDCl3): δ 7670 (t, J=7.83 Hz, 1H), 7.60-7.54 (m, 3H), 4.03 (dd, J=11.35 and 4.30 Hz, 2H), 3.42 (td, J=11.74 and 2.35 Hz, 2H), 2.80-2.63 (m, 1H), 1.72 (m, 4H).

EXAMPLE 12

3-Isobutyl-1-(4-(6-(piperidin-1-ylmethyl)pyridin-2-yl)benzyl)imidazolidine-2,4-dione

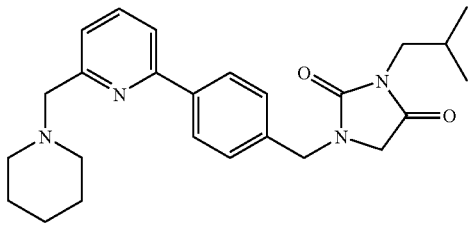

i) To a solution of 1-(4-bromobenzyl)-3-isobutylimidazolidine-2,4-dione (Example 1, step i)) (2.0 g, 6.2 mmol), bis(pinacolato)diboron 1.6 g, 6.2 mmol) and potassium acetate (1.8 g, 18.5 mmol) in DMF (50 ml) under a nitrogen atmosphere was added 1,1'-bis(diphenylphosphino)ferrocenedichloro palladium(II) (134 mg, 0.18 mmol). After 17 h stirring at 75° C. the reaction mixture was cooled to room temperature. Water was added and the product was extracted into ethylacetate. The combined organic phases were washed with a saturated aqueous solution of sodium hydrogen carbonate, water, brine, dried over sodium sulfate and concentrated under reduced pressure to afford 3-Isobutyl-1-(4-(4,4,5,5-tetramethyl-(1,3,2)dioxaborolan-2-yl)benzyl)imidazolidine-2,4-dione (6.8 g) as a black oil. The product was used in the following step without further purification.

ii) To a solution of the product obtained in the previous step (1.31 g, 3.52 mmol) and 2-bromo-6-(piperidin-1-ylmethyl)pyridine (example 5) (748 mg, 2.93 mmol) in toluene/ethanol (4/1, 25 ml) was added an aqueous solution of 2M potassium carbonate. After 15 minutes stirring under a nitrogen atmosphere, tetrakis(triphenylphosphine)palladium(0) (85 mg, 0.073 mmol) was added and this mixture was stirred for 17 h at 75° C. under a nitrogen atmosphere. After completion, the mixture was cooled to room temperature and filtered through decalite. Water was added to the filtrate and the product was extracted into ethylacetate. The combined organic phases were washed with water, brine, dried over sodium sulfate and concentrated under reduced pressure. Column chromatography afforded 3-Isobutyl-1-(4-(6-(piperidin-1-ylmethyl)pyridin-2-yl)benzyl)imidazolidine-2,4-dione (120 mg) as a white solid.

1H NMR (400 MHz, CDCl3): δ 8.00 (d, J=8.22 Hz, 2H), 7.72 (dd, J=8.22 and 7.83 Hz, 1H), 7.56 (d, J=8.22 Hz, 1H), 7.43 (d, J=7.83 Hz, 1H), 7.34 (d, J=8.22 Hz, 2H), 4.62 (s, 2H), 3.74 (s, 2H), 3.72 (s, 2H), 3.36 (d, J=7.43 Hz, 2H), 2.53-2.47 (m, 4H), 1.65-1.58 (m, 4H), 1.50-1.42 (m, 2H), 2.15-2.05 (m, 1H), 0.93 (d, J=6.65 Hz, 6H).

Following a procedure analogous to that described in Example 12 the following compounds were prepared:

| | Examples | Starting materials |
|---|---|---|
| 13 | 3-isobutyl-1-(4-(6-(morpholinomethyl)pyridin-2-yl)benzyl)imidazolidine-2,4-dione<br>1H NMR (400 MHz, CDCl3): δ 7.99 (d, J = 8.61 Hz, 2H), 7.62 (dd, J = 7.83 and 7.43 Hz, 1H), 7.59 (d, J = 7.83 Hz, 1H), 7.43 (d, J = 7.43 Hz, 1H), 7.35 (d, J = 8.22 Hz, 2H), 4.62 (s, 2H), 3.76 (s, 2H), 3.75 (s, 2H), 3.37 (d, J = 7.43 Hz, 2H), 2.61-2.56 (m, 4H), 2.14-2.05 (m, 1H), 1.59-1.53 (m, 4H), 0.93 (d, J = 6.65 Hz, 6H). | 1, 6B |
| 14 | 1-(4-(5-Fluoro-6-((tetrahydro-2H-pyran-4-ylamino)methyl)pyridin-2-yl)benzyl)-3-isobutylimidazolidine-2,4-dione<br>1H NMR (400 MHz, CDCl3): δ 7.95 (d, J = 8.61 Hz, 2H), 7.62 (dd, J = 8.61 and 3.52 Hz, 1H), 7.43 (dd, J = 9.00 and 8.61 Hz, 1H), | 1, 7I |

| Examples | Starting materials |
|---|---|
| 7.35 (d, J = 8.61 Hz, 2H), 4.63 (s, 2H), 4.08 (s, 2H), 4.04-3.97 (m, 2H), 3.76 (s, 2H), 3.49 (d, J = 3.13 Hz, 1H), 3.42 (td, J = 11.7 and 2.35 Hz, 2H), 3.37 (d, J = 7.43 Hz, 2H), 2.83-2.73 (m, 1H), 2.17-2.04 (m, 1H), 1.95-1.87 (m, 2H), 1.62-1.47 (m, 1H), 0.93 (d, J = 6.65 Hz, 6H). | |
| 15 1-(4-(6-((1,1-Dioxo-1$\lambda^6$-thiomorpholin-4-yl)methyl)pyridin-2-yl)benzyl)-3-isobutylimidazolidine-2,4-dione<br>$^1$H NMR (400 MHz, CDCl$_3$): δ 7.98 (d, J = 8.61 Hz, 2H), 7.77 (dd, J = 7.83 and 7.43 Hz, 1H), 7.63 (d, J = 7.83 Hz, 1H), 7.36 (m, 3H), 4.63 (s, 2H), 3.92 (s, 2H), 3.76 (s, 2H), 3.37 (d, J = 7.43 Hz, 2H), 3.18-3.09 (m, 8H), 2.15-2.04 (m, 1H), 0.93 (d, J = 6.65 Hz, 6H). | 1, 6A |
| 16 1-(4-(6-((1,1-Dioxo-1$\lambda^6$-thiomorpholin-4-yl)methyl)-5-fluoropyridin-2-yl)benzyl)-3-isobutylimidazolidine-2,4-dione<br>$^1$H NMR (400 MHz, CDCl$_3$): δ 7.94 (d, J = 8.22 Hz, 2H), 7.68 (dd, J = 8.61 and 3.52 Hz, 1H), 7.48 (dd, J = 9.00 and 8.61 Hz, 1H), 7.36 (d, J = 8.22 Hz, 2H), 4.62 (s, 2H), 4.02 (d, J = 2.35 Hz, 2H), 3.76 (s, 2H), 3.37 (s, 2H), 3.24-3.18 (m, 4H), 3.13-3.06 (m, 4H), 2.14-2.04 (m, 1H), 0.93 (d, J = 7.04 Hz, 6H). | 1, 7A |
| 17 1-(4-(5-Fluoro-6-((3-methylpiperidin-1-yl)methyl)pyridin-2-yl)benzyl)-3-isobutylimidazolidine-2,4-dione<br>$^1$H NMR (400 MHz, CDCl$_3$): δ 7.96 (d, J = 8.22 Hz, 2H), 7.62 (dd, J = 8.61 and 3.52 Hz, 1H), 7.43 (dd, J = 9.00 and 8.61 Hz, 1H), 7.34 (d, J = 8.22 Hz, 2H), 4.62 (s, 2H), 3.83 (bs, 2H), 3.76 (s, 2H), 3.37 (d, J = 7.43 Hz, 2H), 3.06-2.94 (m, 2H), 2.15-2.02 (m, 2H), 1.81-1.55 (m, 6H), 0.93 (d, J = 7.04 Hz, 6H), 0.85 (d, J = 5.87 Hz, 3H). | 1, 7C |
| 18 1-(4-(6-((3,3-Difluoro-piperidin-1-yl)methyl)-5-fluoro-pyridin-2-yl)benzyl)-3-isobutylimidazolidine-2,4-dione<br>$^1$H NMR (400 MHz, CDCl$_3$): δ 7.96 (d, J = 8.22 Hz, 2H), 7.66 (dd, J = 8.61 and 3.52 Hz, 1H), 7.46 (dd, J = 1, 9.00 and 8.61 Hz, 1H), 7.35 (d, J = 8.22 Hz, 2H), 4.62 (s, 2H), 3.99 (d, J = 2.35 Hz, 2H), 3.76 (s, 2H), 3.37 (d, J = 7.43 Hz, 2H), 2.88 (t, J = 11.35 Hz, 2H), 2.69-2.62 (m, 2H), 2.17-2.05 (m, 1H), 1.92-1.74 (m, 4H), 0.93 (d, J = 6.65 Hz, 6H). | 1, 7F |
| 19 1-(4-(5-Fluoro-6-((3-fluoro-piperidin-1-yl)methyl)pyridin-2-yl)benzyl)-3-isobutylimidazolidine-2,4-dione<br>$^1$H NMR (400 MHz, CDCl$_3$): δ 7.96 (d, J = 8.22 Hz, 2H), 7.64 (dd, J = 8.61 and 3.52 Hz, 1H), 7.44 (dd, J = 9.00 and 8.61 Hz, 1H), 7.35 (d, J = 8.22 Hz, 2H), 4.62 (s, 2H), 3.86 (d, J = 2.35 Hz, 2H), 3.76 (s, 2H), 3.37 (d, J = 7.43 Hz, 2H), 2.84-2.75 (m, 2H), 2.64-2.54 (m, 2H), 2.17-1.85 (m, 6H), 0.93 (d, J = 6.65 Hz, 6H). | 1, 7G |
| 20 1-(4-(5-Fluoro-6-((3-trifluoromethyl-piperidin-1-yl)methyl)pyridin-2-yl)benzyl)-3-isobutylimidazolidine-2,4-dione<br>$^1$H NMR (400 MHz, CDCl$_3$): δ 7.94 (d, J = 8.22 Hz, 2H), 7.64 (dd, J = 8.61 and 3.52 Hz, 1H), 7.45 (dd, J = 9.00 and 8.61 Hz, 1H), 7.34 (d, J = 8.22 Hz, 2H), 4.62 (s, 2H), 3.88 (bs, 2H), 3.76 (s, 2H), 3.37 (d, J = 7.04 Hz, 2H), 3.32-3.25 (m, 1H), 3.09-3.01 (m, 1H), 2.46-2.34 (m, 1H), 2.23-2.04 (m, 3H), 1.98-1.88 (m, 1H), 1.79-1.68 (m, 1H), 1.31-1.21 (m, 2H), 0.93 (d, J = 6.65 Hz, 6H). | 1, 7H |
| 21 1-(4-(6-((Cyclohexyl)amino)methyl-5-fluoro-pyridin-2-yl)benzyl)-3-isobutylimidazolidine-2,4-dione<br>$^1$H NMR (400 MHz, CDCl$_3$): δ 7.96 (d, J = 8.22 Hz, 2H), 7.60 (dd, J = 8.61 and 3.52 Hz, 1H), 7.41 (dd, J = 9.00 and 8.61 Hz, 1H), 7.35 (d, J = 8.22 Hz, 2H), 4.62 (s, 2H), 4.07 (d, J = 1.96 Hz, 2H), 3.77 (s, 2H), 3.37 (d, J = 7.43 Hz, 2H), 2.57-2.47 (m, 1H), 2.16-2.04 (m, 1H), 2.02-1.94 (m, 2H), 1.81-1.72 (m, 2H), 1.67-1.59 (m, 1H), 1.33-1.13 (m, 5H), 0.93 (d, J = 6.65 Hz, 6H). | 1, 7J |
| 22 3-Isobutyl-1-(4-(6-((tetrahydro-2H-pyran-4-ylamino)methyl)pyridin-2-yl)benzyl)imidazolidine-2,4-dione<br>$^1$H NMR (400 MHz, CDCl$_3$): δ 8.00 (d, J = 8.61 Hz, 2H), 7.72 (dd, J = 7.83 and 7.43 Hz, 1H), 7.59 (d, J = 7.83 Hz, 1H) 7.36 (d, J = 8.61 Hz, 2H), 7.26 (d, J = 7.43 Hz, 1H) 4.63 (s, 2H), 4.04-3.96 (m, 4H), 3.76 (s, 2H), 3.42 (Td, 11.74 and 1.96 Hz, 2H), 3.83 (d, J = 2.74 Hz, 2H), 2.62-2.53 (m, 4H), 2.25 (s, 3H), 1.65-1.55 (m, 4H), 1.47-1.38 (m, 2H). | 1, 6H |
| 23 1-(4-(5-Fluoro-6-((tetrahydro-2H-pyran-4-yloxy)methyl)pyridin-2-yl)benzyl)-3-isobutylimidazolidine-2,4-dione<br>$^1$H NMR (400 MHz, CDCl$_3$): δ 7.96 (d, J = 8.22 Hz, 2H), 7.68 (dd, J = 8.61 and 3.52 Hz, 1H), 7.47 (d, J = 9.00 and 8.61 Hz, 1H), 7.34 (d, J = 8.22 Hz, 2H), 4.79 (d, J = 1.96 Hz, 2H), 4.62 (s, 2H), 4.01-3.77 (m, 2H), 3.79-3.70 (m, 3H), 3.50-3.41 (m, 2H), 3.37 (d, J = 7.43 Hz, 2H), 2.15-2.05 (m, 1H), 1.76-1.62 (m, 2H), 0.93 (d, J = 6.65 Hz, 6H). | 1, 9 |
| 24 1-(4-(5-Fluoro-6-(piperidin-1-ylmethyl)pyridin-2-yl)benzyl)-3-methylimidazolidine-2,4-dione<br>$^1$H NMR (400 MHz, CDCl$_3$): δ 7.96 (d, J = 8.22 Hz, 2H), 7.62 (dd, J = 8.61 and 3.52 Hz, 1H), 7.42 (dd, J = 9.00 and 8.61 Hz, 1H), | 2A, 7D |

| Examples | Starting materials |
|---|---|
| 7.35 (d, J = 8.22 Hz, 2H), 4.62 (s, 2H), 3.82 (d, J = 2.35 Hz, 2H), 3.76 (s, 2H), 3.07 (s, 3H), 2.61-2.54 (m, 4H), 1.64-1.57 (m, 4H), 1.45-1.37 (m, 2H). | |
| 25  3-ethyl-1-(4-(6-(piperidin-1-ylmethyl)pyridin-2-yl)benzyl)imidazolidine-2,4-dione<br>$^1$H NMR (400 MHz, CDCl$_3$): δ 7.99 (d, J = 8.22 Hz, 2H), 7.74 (dd, J = 7.83 and 7.43 Hz, 1H), 7.61 (d, J = 7.83 Hz, 1H), 7.45 (d, J = 7.43 Hz, 1H), 7.35 (d, J = 8.22 Hz, 2H), 4.61 (s, 2H), 3.72 (bs, 4H), 3.61 (q, J = 7.04 Hz, 2H), 2.53-2.47 (m, 4H), 1.65-1.57 (m, 4H), 1.50-1.43 (m, 2H), 1.25 (t, 3H). | 2B, 5 |
| 26  3-ethyl-1-(4-(5-fluoro-6-(piperidin-1-ylmethyl)pyridin-2-yl)benzyl)imidazolidine-2,4-dione<br>$^1$H NMR (400 MHz, CDCl$_3$): δ 7.97 (d, J = 8.22 Hz, 2H), 7.63 (dd, J = 8.61 and 3.52 Hz, 1H), 7.43 (dd, J = 9.00 and 8.61 Hz, 1H), 7.35 (d, J = 8.61 Hz, 2H), 4.61 (s, 2H), 3.85 (d, J = 2.35 Hz, 2H), 3.74 (s, 2H), 3.61 (q, J = 7.43 Hz, 2H), 2.62 (bs, 4H), 1.66-1.57 (m, 4H), 1.47-1.38 (m, 2H), 1.25 (t, J = 7.43 Hz, 3H). | 2B, 7D |
| 27  1-(4-(6-(1,1-Dioxo-1λ$^6$-thiomorpholin-4-ylmethyl)-5-fluoropyridin-2-yl)benzyl)-3-ethylimidazolidine-2,4-dione<br>$^1$H NMR (400 MHz, CDCl$_3$): δ 7.94 (d, J = 8.22 Hz, 2H), 7.69 (dd, J = 8.61 and 3.52 Hz, 1H), 7.49 (dd, J = 9.00 and 8.61 Hz, 1H), 7.36 (d, J = 8.22 Hz, 2H), 4.62 (s, 2H), 4.02 (d, J = 2.35 Hz, 2H), 3.75 (s, 2H), 3.60 (q, J = 7.43 Hz, 2H), 3.26-3.17 (m, 4H), 3.14-3.04 (m, 4H), 1.25 (t, J = 7.43 Hz, 3H). | 2B, 7A |
| 28  1-(4-(6-(1,1-dioxo-1λ$^6$-thiomorpholin-4-ylmethyl)pyridin-2-yl)benzyl)-3-ethylimidazolidine-2,4-dione<br>$^1$H NMR (400 MHz, CDCl$_3$): δ 7.98 (d, J = 8.22 Hz, 2H), 7.77 (dd, J = 7.83 and 7.43 Hz, 1H), 7.63 (d, J = 7.83 Hz, 1H), 7.39-7.34 (m, 2H), 4.62 (s, 2H), 3.93 (s, 2H), 3.73 (s, 2H), 3.61 (q, J = 7.04 Hz, 2H), 3.19-3.08 (m, 8H), 1.25 (t, J = 7.04 Hz, 3H). | 2B, 6A |
| 29  1-((6-(4-((3-ethyl-2,4-dioxoimidazolidin-1-yl)methyl)phenyl)-3-fluoropyridin-2-yl)methyl)piperidine-3-carbonitrile<br>$^1$H NMR (400 MHz, CDCl$_3$): δ 7.96 (d, J = 8.22 Hz, 2H), 7.65 (dd, J = 8.61 and 3.52 Hz, 1H), 7.45 (dd, J = 9.00 and 8.61 Hz, 1H), 7.36 (d, J = 8.22 Hz, 2H), 4.62 (s, 2H), 3.90 (d, J = 2.35 Hz, 2H), 3.74 (s, 2H), 3.61 (q, J = 7.04 Hz, 2H), 3.03-2.95 (m, 1H), 2.84-2.72 (m, 2H), 2.71-2.65 (m, 1H), 2.55-2.46 (m, 1H), 1.94-1.76 (m., 2H), 1.70-1.58 (m, 2H), 1.25 (t, J = 7.04 Hz, 3H). | 2B, 7K |
| 30  1-(4-(6-(cyclohexylmethyl)pyridin-2-yl)benzyl)-3-ethylimidazolidine-2,4-dione<br>$^1$H NMR (400 MHz, CDCl$_3$): δ 7.99 (d, J = 8.22 Hz, 2H), 7.64 (dd, J = 7.83 and 7.43 Hz, 1H), 7.50 (d, J = 7.83 Hz, 1H), 7.35 (d, J = 8.22 Hz, 2H), 7.05 (d, J = 7.43 Hz, 1H), 4.62 (s, 2H), 3.73 (s, 2H), 3.61 (q, J = 7.43 Hz, 2H), 2.72 (d, J = 7.04 Hz, 2H), 1.92-1.78 (m, 1H), 1.76-1.58 (m, 6H), 1.31-1.15 (m, 5H), 1.10-0.98 (m, 2H). | 2B, 10 |
| 31  1-(4-(5-Fluoro-6-(piperidin-1-ylmethyl)pyridin-2-yl)benzyl)-3-propylimidazolidine-2,4-dione<br>$^1$H NMR (400 MHz, CDCl$_3$): δ 7.96 (d, J = 8.61 Hz, 2H), 7.63 (dd, J = 8.61 and 3.52 Hz, 1H), 7.43 (dd, J = 9.00 and 8.61 Hz, 1H), 7.34 (d, J = 8.61 Hz, 2H), 4.61 (s, 2H), 3.74 (s, 2H), 3.51 (t, J = 7.04 Hz, 2H), 3.49 (s, 2H), 2.70-2.51 (m, 4H), 1.76-1.55 (m, 6H), 1.49-1.35 (m, 2H), 0.94 (t, J = 7.04 Hz, 3H). | 2C, 7D |
| 32  1-(4-(6-(Piperidin-1-ylmethyl)pyridin-2-yl)benzyl)-3-propylimidazolidine-2,4-dione<br>$^1$H NMR (400 MHz, CDCl$_3$): δ 7.99 (d, J = 8.22 Hz, 2H), 7.22 (dd, J = 7.83 and 7.04 Hz, 1H), 7.56 (d, J = 7.83 Hz, 1H) 7.43 (d, J = 7.04 Hz, 1H), 7.34 (d, J = 8.22 Hz, 2H), 4.61 (s, 2H), 3.73 (s, 2H), 3.71 (s, 2H), 3.51 (t, J = 7.43 Hz, 2H), 2.53-2.47 (m, 4H), 1.73-1.56 (m, 6H), 1.50-1.42 (m, 2H), 0.94 (t, J = 7.43 Hz, 3H). | 2C, 5 |
| 33  3-Propyl-1-(4-(6-(((tetrahydro-2H-pyran-4-ylamino)methyl)pyridin-2-yl)benzyl)imidazolidine-2,4-dione<br>$^1$H NMR (400 MHz, CDCl$_3$): δ 8.00 (d, J = 8.61 Hz, 2H), 7.72 (dd, J = 7.83 and 7.43 Hz, 1H), 7.59 (d, J = 7.83 Hz, 1H), 7.36 (d, J = 8.61 Hz, 2H), 7.26 (d, J = 7.43 Hz, 1H) 4.62 (s, 2H), 4.04-3.97 (m, 4H), 3.75 (s, 2H), 3.54-3.44 (m, 2H), 3.42 (Td, J = 11.35 and 2.35 Hz, 2H), 2.84-2.74 (m, 1H), 1.94-1.87 (m, 2H), 1.74-1.62 (m, 2H), 1.57-1.46 (m, 2H), 0.94 (t, J = 7.43 Hz, 3H). | 2C, 6H |
| 34  1-(4-(5-Fluoro-6-((tetrahydro-2H-pyran-4-ylamino)methyl)pyridin-2-yl)benzyl)-3-propylimidazolidine-2,4-dione<br>$^1$H NMR (400 MHz, CDCl$_3$): δ 7.95 (d, J = 8.61 Hz, 2H), 7.61 (dd, J = 8.61 and 3.91 Hz, 1H), 7.43 (dd, J = 9.00 and 8.61 Hz, 1H), 7.35 (d, J = 8.61 Hz, 2H), 4.62 (s, 2H), 4.08 (d, J = 1.96 Hz, 2H), 4.04-3.98 (m, 2H), 3.75 (s, 2H), 3.54-3.48 (m, 2H), 3.42 (Td, J = 11.74 and 2.35 Hz, 2H), 2.83-2.74 (m, 1H), 1.95-1.88 (m, 2H), 1.73-1.63 (m, 2H), 1.56-1.49 (m, 2H), 0.95 (t, J = 7.43 Hz, 3H). | 2C, 7I |

| | Examples | Starting materials |
|---|---|---|
| 35 | 1-(4-(6-(1,1-Dioxo-1λ⁶-thiomorpholin-4-ylmethyl-5-fluoropyridin-2-yl)benzyl)-3-propylimidazolidine-2,4-dione<br>¹H NMR (400 MHz, CDCl₃): δ 7.94 (d, J = 8.22 Hz, 2H), 7.68 (dd, J = 8.61 and 3.91 Hz, 1H), 7.48 (d, J = 9.00 and 8.61 Hz, 1H), 7.36 (d, J = 8.22 Hz, 2H), 4.62 (s, 2H), 4.02 (d, J = 2.35 Hz, 2H), 3.75 (s, 2H), 3.54-3.49 (m, 2H), 3.25-3.19 (m, 4H), 3.13-3.07 (m, 4H), 1.73-1.64 (m, 2H), 0.95 (t, J = 7.43 Hz, 3H). | 2C, 7A |
| 36 | 1-(4-(6-(1,1-Dioxo-1 λ⁶-thiomorpholin-4-ylmethyl)pyridin-2-yl)benzyl)-3-propylimidazolidine-2,4-dione<br>¹H NMR (400 MHz, CDCl₃): δ 7.98 (d, J = 8.22 Hz, 2H), 7.77 (dd, J = 7.83 and 7.43 Hz, 1H), 7.63 (d, J = 7.83 Hz, 1H), 7.36 (m, 3H), 4.62 (s, 2H), 3.92 (s, 2H), 3.74 (s, 2H), 3.54-3.48 (m, 2H), 3.18-3.07 (m, 8H), 1.74-1.63 (m, 2H), 0.94 (t, J = 7.43 Hz, 3H). | 2C, 6A |
| 37 | 3-propyl-1-(4-(6-((tetrahydro-2H-pyran-3-ylamino)methyl)pyridin-2-yl)benzyl)imidazolidine-2,4-dione<br>¹H NMR (400 MHz, CDCl₃): δ 8.00 (d, J = 8.22 Hz, 2H), 7.71 (dd, J = 8.22 and 7.43 Hz, 1H), 7.58 (d, J = 7.83 Hz, 1H), 7.35 (d, J = 8.22 Hz, 2H), 7.25 (d, J = 7.43 Hz, 1H), 4.62 (s, 2H), 4.02-3.95 (m, 3H), 3.85-3.78 (m, 1H), 3.75 (s, 2H), 3.54-3.40 (m, 3H), 3.27 (dd, J = 10.46 and 8.61 Hz, 1H), 2.79-2.70 (m, 1H), 2.09-1.94 (m, 2H), 1.748-1.56 (m, 4H), 1.52-1.39 (m, 1H), 0.94 (t, J = 7.43 Hz, 3H). | 2C, 6J |
| 38 | 3-(2,2-Difluoroethyl)-1-(4-(6-(piperidin-1-ylmethyl)pyridin-2-yl)benzyl)imidazolidine-2,4-dione<br>¹H NMR (400 MHz, CDCl₃): δ 8.00 (d, J = 8.61 Hz, 2H), 7.73 (dd, J = 7.83 and 7.42 Hz, 1H), 7.56 (d, J = 7.83 Hz, 1H), 7.44 (d, J = 7.43 Hz, 1H), 7.35 (d, J = 8.61 Hz, 2H), 6.05 (Tt, J = 55.6 and 4.30 Hz, 1H), 4.63 (s, 2H), 3.92 (Td, J = 13.7 and 4.30 Hz, 2H), 3.81 (s, 2H), 3.72 (s, 2H), 2.54-2.40 (m, 4H), 1.67-1.56 (m, 4H), 1.50-1.41 (m, 2H). | 2D, 5 |
| 39 | 3-(2,2-Difluoroethyl)-1-(4-(5-fluoro-6-(piperidin-1-ylmethyl)pyridin-2-yl)benzyl)imidazolidine-2,4-dione<br>¹H NMR (400 MHz, CDCl₃): δ 7.98 (d, J = 8.61 Hz, 2H), 7.62 (dd, J = 8.61 and 3.52 Hz, 1H), 7.43 (dd, J = 9.00 and 8.61 Hz, 1H), 7.37 (d, J = 8.61 Hz, 2H), 4.05 (Tt, J = 55.95 and 4.30 Hz, 1H), 4.63 (s, 2H), 3.92 (Td, J = 13.69 and 4.30 Hz, 2H), 3.83 (s, 2H), 3.82 (s, 2H), 2.63-2.55 (m, 4H), 1.65-1.55 (m, 4H), 1.45-1.37 (m, 2H). | 2D, 7D |
| 40 | 3-(Cyclopropylmethyl)-1-(4-(5-fluoro-6-(Piperidin-1-ylmethyl)pyridin-2-yl)benzyl)imidazolidine-2,4-dione<br>¹H NMR (400 MHz, CDCl₃): δ 7.97 (d, J = 8.22 Hz, 2H), 7.62 (dd, J = 8.61 and 3.52 Hz, 1H), 7.42 (t, J = 8.61 Hz, 1H), 7.35 (d, J = 8.22 Hz, 2H), 4.62 (s, 2H), 3.82 (d, J = 2.74 Hz, 2H), 3.76 (s, 2H), 3.41 (d, J = 7.01 Hz, 2H), 2.61-2.55 (m, 4H), 1.64-1.56 (m, 4H), 1.45-1.38 (m, 2H), 1.23-1.16 (m, 1H), 0.55-0.48 (m, 2H), 0.39-0.34 (m, 2H). | 2E, 7D |
| 41 | 3-Cyclopropylmethyl-1-(4-(6-(piperidin-1-ylmethyl)pyridin-2-yl)benzyl)imidazolidine-2,4-dione<br>¹H NMR (400 MHz, CDCl₃): δ 7.99 (d, J = 8.22 Hz, 2H), 7.72 (dd, J = 8.22 and 7.83 Hz, 1H), 7.56 (d, J = 8.22 Hz, 1H), 7.43 (d, J = 7.83 Hz, 1H), 7.35 (d, J = 8.22 Hz, 2H), 4.62 (s, 2H), 3.75 (s, 2H), 3.72 (s, 2H), 3.41 (d, J = 7.04 Hz, 2H), 2.53-2.47 (m, 4H), 1.654-1.58 (m, 4H), 1.52-1.42 (m, 2H), 1.24-1.14 (m, 1H), 0.56-0.47 (m, 2H), 0.40-0.33 (m, 2H). | 2E, 5 |
| 42 | 3-Cyclobutylmethyl-1-(4-(5-fluoro-6-(piperidin-1-ylmethyl)pyridin-2-yl)benzyl)imidazolidine-2,4-dione<br>¹H NMR (400 MHz, CDCl₃): δ 7.96 (d, J = 8.22 Hz, 2H), 7.62 (dd, J = 8.61 and 3.52 Hz, 1H), 7.42 (t, J = 8.61 Hz, 1H), 7.33 (d, J = 8.22 Hz, 2H), 4.60 (s, 2H), 3.82 (d, J = 2.74 Hz, 2H), 3.73 (s, 2H), 3.58 (d, J = 7.43 Hz, 2H), 2.76-2.66 (m, 1H), 2.63-2.53 (m, 4H), 2.09-1.99 (m, 2H), 1.93-1.84 (m, 2H), 1.83-1.75 (m, 2H), 1.64-1.57 (m, 4H), 1.47-1.37 (m, 2H). | 2F, 7D |
| 43 | 3-Cyclobutylmethyl-1-(4-(6-(piperidin-1-ylmethyl)pyridin-2-yl)benzyl)imidazolidine-2,4-dione<br>¹H NMR (400 MHz, CDCl₃): δ 7.98 (d, J = 8.22 Hz, 2H), 7.62 (dd, J = 8.22 and 7.83 Hz, 1H), 7.56 (d, J = 8.22 Hz, 1H), 7.43 (d, J = 7.83 Hz, 1H), 7.33 (d, J = 8.22 Hz, 2H), 4.61 (s, 2H), 3.72 (bs, 4H), 3.58 (d, J = 7.43 Hz, 2H), 2.76-2.66 (m, 1H), 2.54-2.46 (m, 4H), 2.09-1.98 (m, 2H), 1.93-1.75 (m, 4H), 1.66-1.56 (m, 4H), 1.51-1.41 (m, 2H). | 2F, 5 |
| 44 | 3-(2-Methoxyethyl)-1-(4-(6-(piperidin-1-ylmethyl)pyridin-2-yl)benzyl)imidazolidine-2,4-dione<br>¹H NMR (400 MHz, CDCl₃): δ 7.99 (d, J = 8.22 Hz, 2H), 7.72 (dd, J = 7.83 and 7.43 Hz, 1H), 7.57 (d, J = 7.83 Hz, 1H), 7.43 (d, J = 7.43 Hz, 1H), 7.35 (d, J = 8.22 Hz, 2H), 4.62 (s, 2H), 3.78-3.73 (m, 6H), 3.61 (t, J = 5.48 Hz, 2H), 3.37 (s, 3H), 2.52 (bs, 4H), 1.67-1.59 (m, 4H), 1.51-1.43 (m, 2H). | 2G, 5 |

| | Examples | Starting materials |
|---|---|---|
| 45 | 1-(4-(5-Fluoro-6-(piperidin-1-ylmethyl)pyridin-2-yl)benzyl)-3-(2-methoxy-ethyl)imidazolidine-2,4-dione<br>$^1$H NMR (400 MHz, CDCl$_3$): δ 7.96 (d, J = 8.22 Hz, 2H), 7.63 (dd, J = 8.61 and 3.53 Hz, 1H), 7.43 (dd, J = 9.00 and 8.61 Hz, 1H), 7.35 (d, J = 8.22 Hz, 2H), 4.62 (s, 2H), 3.83 (s, 2H), 3.78 (s, 2H), 3.76 (t, J = 5.48 Hz, 2H), 3.61 (t, J = 5.48 Hz, 2H), 3.30 (s, 3H), 2.62-2.55 (m, 4H), 1.65-1.55 (m, 4H), 1.45-1.37 (m, 2H). | 2G, 7D |
| 46 | (2,5-Dioxo-3-(4-(6-(piperidin-1-ylmethyl)pyridin-2-yl)benzyl)imidazolidin-1-yl)acetic acid methyl ester<br>$^1$H NMR (400 MHz, CDCl$_3$): δ 8.00 (d, J = 8.61 Hz, 2H), 7.72 (dd, J = 7.83 and 7.43 Hz, 1H), 7.56 (d, J = 7.83 Hz, 1H), 7.43 (d, J = 7.43 Hz, 1H), 7.35 (d, J = 8.61 Hz, 2H), 4.65 (s, 2H), 4.31 (s, 2H), 3.83 (s, 2H), 3.79 (s, 3H), 3.72 (s, 2H), 2.54-2.47 (m, 4H), 1.65-1.58 (m, 4H), 1.50-1.43 (m, 2H). | 2H, 5 |
| 47 | (3-(4-(5-Fluoro-6-(piperidin-1-ylmethyl)pyridin-2-yl)benzyl)-2,5-dioxo-imidazolidin-1-yl)acetic acid methyl ester<br>$^1$H NMR (400 MHz, CDCl$_3$): δ 7.97 (d, J = 8.22 Hz, 2H), 7.63 (dd, J = 8.61 and 3.52 Hz, 1H), 7.43 (dd, J = 9.00 and 8.61 Hz, 1H), 7.35 (d, J = 8.22 Hz, 2H), 4.65 (s, 2H), 4.32 (s, 2H), 3.85 (s, 4H), 3.79 (s, 3H), 2.67-2.56 (m, 4H), 1.65-1.56 (m, 4H), 1.46-1.38 (m, 2H). | 2H, 7D |
| 48 | 3-(2-Oxopropyl)-1-(4-(6-(piperidin-1-ylmethyl)pyridin-2-yl)benzyl)imidazolidine-2,4-dione<br>$^1$H NMR (400 MHz, CDCl$_3$): δ 8.00 (d, J = 8.22 Hz, 2H), 7.73 (dd, J = 7.83 and 7.43 Hz, 1H), 7.56 (d, J = 7.83 Hz, 1H) 7.43 (d, J = 7.43 Hz, 1H), 7.36 (d, J = 8.22 Hz, 2H), 4.64 (s, 2H), 4.36 (s, 2H), 3.85 (s, 2H), 3.72 (s, 2H), 2.54-2.46 (m, 4H), 2.25 (s, 3H), 1.66-1.58 (m, 4H), 1.50-1.42 (m, 2H). | 2I, 5 |
| 49 | 1-(4-(5-Fluoro-6-(piperidin-1-ylmethyl)pyridin-2-yl)benzyl)-3-(2-oxopropyl)imidazolidine-2,4-dione<br>$^1$H NMR (400 MHz, CDCl$_3$): δ 7.98 (d, J = 8.22 Hz, 2H), 7.62 (dd, J = 8.61 and 3.52 Hz, 1H), 7.43 (dd, J = 9.00 and 8.61 Hz, 1H) 7.36 (d, J = 8.22 Hz, 1H), 4.64 (s, 2H), 4.37 (s, 2H), 3.86 (s, 2H), 3.83 (d, J = 2.74 Hz, 2H), 2.62-2.53 (m, 4H), 2.25 (s, 3H), 1.65-1.55 (m, 4H), 1.47-1.38 (m, 2H). | 2I, 7D |
| 50 | 1-(4-(6-(1,1-Dioxo-1λ$^6$-thiomorpholin-4-ylmethyl)-5-fluoropyridin-2-yl)benzyl)-3-(2-oxopropyl)imidazolidine-2,4-dione<br>$^1$H NMR (400 MHz, CDCl$_3$): δ 7.95 (d, J = 8.22 Hz, 2H), 7.68 (dd, J = 8.61 and 3.52 Hz, 1H), 7.48 (d, J = 9.00 and 8.61 Hz, 1H), 7.37 (d, J = 8.22 Hz, 2H), 4.65 (s, 2H), 4.37 (s, 2H), 4.02 (d, J = 2.74 Hz, 2H), 3.86 (s, 2H), 3.24-3.19 (m, 4H), 3.13-3.07 (m, 4H), 2.26 (s, 3H). | 2I, 7A |
| 51 | 3-(2-Oxo-propyl)-1-(4-(6-((tetrahydro-2H-pyran-4-ylamino)methyl)pyridin-2-yl)benzyl)imidazolidine-2,4-dione<br>$^1$H NMR (400 MHz, CDCl$_3$): δ 8.01 (d, J = 8.61 Hz, 2H), 7.72 (dd, J = 7.83 and 7.43 Hz, 1H), 7.59 (d, J = 7.83 Hz, 1H), 7.37 (d, J = 8.61 Hz, 2H), 7.25 (d, J = 7.43 Hz, 1H), 4.65 (s, 2H), 4.37 (s, 2H), 4.05-3.97 (m, 4H), 3.86 (s, 2H), 3.42 (Td, J = 11.74 and 2.35 Hz, 2H), 2.84-2.75 (m, 1H), 2.25 (s, 3H), 1.94-1.87 (m, 2H), 1.58-1.48 (m, 2H). | 2I, 6H |
| 52 | 1-(4-(5-Fluoro-6-((tetrahydro-2H-pyran-4-ylamino)methyl)pyridin-2-yl)benzyl)-3-(2-oxo-propyl)imidazolidine-2,4-dione<br>$^1$H NMR (400 MHz, CDCl$_3$): δ 7.97 (d, J = 8.22 Hz, 2H), 7.62 (dd, J = 8.61 and 3.52 Hz, 1H), 7.43 (dd, J = 9.00 and 8.61 Hz, 1H), 7.37 (d, J = 8.22 Hz, 2H), 4.65 (s, 2H), 4.37 (s, 2H), 4.08 (d, J = 2.75 Hz, 2H), 4.04-3.98 (m, 2H), 3.87 (s, 2H), 3.42 (Td, J = 11.74 and 2.35 Hz, 2H), 2.83-2.74 (m, 1H), 2.25 (s, 3H), 1.95-1.88 (m, 2H), 1.56-1.49 (m, 2H). | 2I, 7I |
| 53 | 1-(4-(6-(1,1-Dioxo-1λ$^6$-thiomorpholin-4-ylmethyl)pyridin-2-yl)benzyl)-3-(2-oxo-propyl)imidazolidine-2,4-dione<br>$^1$H NMR (400 MHz, CDCl$_3$): δ 8.00 (d, J = 8.22 Hz, 2H), 7.77 (dd, J = 7.83 and 7.43 Hz, 1H), 7.64 (d, J = 7.83 Hz, 1H), 7.41-7.33 (m, 3H), 4.65 (s, 2H), 4.36 (s, 2H), 3.92 (s, 2H), 3.85 (s, 2H), 3.19-3.08 (m, 8H), 2.26 (s, 3H). | 2I, 6$^a$ |
| 54 | 1-(4-(6-(Difluoro-(tetrahydro-2H-pyran-4-yl)methyl)pyridin-2-yl)benzyl)-3-(2-oxo-propyl)imidazolidine-2,4-dione<br>$^1$H NMR (400 MHz, CDCl$_3$): δ 8.05 (d, J = 8.22 Hz, 2H), 7.87 (dd, J = 8.22 and 7.43 Hz, 1H), 7.80 (d, J = 7.43 Hz, 1H), 7.56 (d, J = 8.22 Hz, 1H), 7.39 (d, J = 8.33 Hz, 2H), 4.62 (s, 2H), 4.37 (s, 2H), 4.05-4.00 (m, 2H), 3.87 (s, 2H), 3.42 (td, J = 11.74 and 2.35 Hz, 2H), 2.91-2.78 (m, 1H), 2.26 (s, 3H), 1.76-1.62 (m, 4H). | 2I, 11 |
| 55 | 3-(2-Oxo-propyl)-1-(4-(6-((tetrahydro-2H-pyran-3-ylamino)methyl)pyridin-2-yl)benzyl)imidazolidine-2,4-dione<br>$^1$H NMR (400 MHz, CDCl$_3$): δ 8.01 (d, J = 8.22 Hz, 2H), 7.72 (dd, J = 8.22 and 7.43 Hz, 1H), 7.59 (d, J = 7.83 Hz, 1H), 7.37 (d, J = 8.22 Hz, 2H), 7.25 (d, J = 7.43 Hz, 1H), 4.65 (s, 2H), 4.37 (s, 2H), 4.02-3.96 (m, 3H), 3.86 (s, 2H), 3.85-3.77 (m, 1H), 3.50-3.39 (m, | 2I, 6J |

-continued

| | Examples | Starting materials |
|---|---|---|
| | 2H), 3.30-3.22 (m, 1H), 2.79-2.70 (m, 1H), 2.25 (s, 3H), 2.07-1.98 (m, 1H), 1.76-1.62 (m, 3H). | |
| 56 | 1-(4-(6-((3-Oxo-piperidin-1-yl)methyl)pyridin-2-yl)benzyl)-3-(2-oxo-propyl)imidazolidine-2,4-dione<br>$^1$H NMR (400 MHz, CDCl$_3$): δ 8.00 (d, J = 8.22 Hz, 2H), 7.74 (dd, J = 7.83 and 7.43 Hz, 1H), 7.60 (d, J = 7.83 Hz, 1H), 7.41-7.35 (m, 3H), 4.65 (s, 2H), 4.37 (s, 2H), 3.85 (bs, 4H), 3.15 (s, 2H), 3.82-2.76 (m, 2H), 2.44-2.37 (m, 2H), 2.25 (s, 3H), 2.05-1.96 (m, 2H). | 2I, 6G |
| 57 | 3-Isopropyl-1-(4-(6-(piperidin-1-ylmethyl)pyridin-2-yl)benzyl)imidazolidine-2,4-dione<br>1H NMR (400 MHz, CDCl3): δ 7.99 (d, J = 8.61 Hz, 2H), 7.72 (dd, J = 7.83 and 7.43 Hz, 1H), 7.56 (d, J = 7.83 Hz, 1H), 7.43 (d, J = 7.43 Hz, 1H), 7.34 (d, J = 8.61 Hz, 2H), 4.58 (s, 2H), 4.40-4.32 (m, 1H), 3.72 (s, 2H), 3.67 (s, 2H), 2.50 (bs, 4H), 1.66-1.57 (m, 6H), 1.44 (d, J = 7.04 Hz, 6H). | 3, 5 |
| 58 | 1-(4-(5-Fluoro-6-(piperidin-1-ylmethyl)pyridin-2-yl)benzyl)-3-isopropylimidazolidine-2,4-dione<br>$^1$H NMR (400 MHz, CDCl$_3$): δ 7.96 (d, J = 8.22 Hz, 2H), 7.62 (dd, J = 7.83 and 3.52 Hz, 1H), 7.42 (dd, J = 9.00 and 8.61 Hz, 1H), 7.34 (d, J = 8.22 Hz, 2H), 4.58 (m, 2H), 4.40-4.31 (m, 1H), 3.83 (s, 2H), 3.67 (s, 2H), 2.62-2.55 (m, 4H), 1.64-1.56 (m, 4H), 1.46-1.38 (m, 8H). | 3, 7D |
| 59 | 1-(4-(6-(1,1-Dioxo-1$\lambda^6$-thiomorpholin-4-ylmethyl)-5-fluoropyridin-2-yl)benzyl)-3-isopropylimidazolidine-2,4-dione<br>$^1$H NMR (400 MHz, DMSO): δ 8.05 (d, J = 8.22 Hz, 2H), 7.99 (dd, J = 8.61 and 3.52 Hz, 1H), 7.81 (dd, J = 9.39 and 8.61 Hz, 1H), 7.39 (d, J = 8.22 Hz, 2H), 4.53 (s, 2H), 4.24-4.15 (m, 1H), 3.95 (bs, 2H), 3.86 (s, 2H), 3.15-3.02 (m, 8H), 1.34 (d, J = 6.65 Hz, 6H). | 3, 7$^a$ |
| 60 | 1-(4-(6-(1,1-Dioxo-1$\lambda^6$-thiomorpholin-4-ylmethyl)pyridin-2-yl)benzyl)-3-isopropylimidazolidine-2,4-dione<br>$^1$H NMR (400 MHz, CDCl$_3$): δ 7.98 (d, J = 8.22 Hz, 2H), 7.77 (dd, J = 7.83 and 7.43 Hz, 1H), 7.63 (d, J = 7.83 Hz, 1H), 7.39-7.32 (m, 3H), 4.60 (s, 2H), 4.41-4.30 (m, 1H), 3.92 (s, 2H), 3.68 (s, 2H), 3.19-3.08 (m, 8H), 1.44 (d, J = 7.04 Hz, 6H). | 3, 6A |
| 61 | 3-Cyclopropyl-1-(4-(5-fluoro-6-(piperidin-1-ylmethyl)pyridin-2-yl)benzyl)imidazolidine-2,4-dione<br>$^1$H NMR (400 MHz, CDCl$_3$): δ 7.96 (d, J = 8.22 Hz, 2H), 7.62 (dd, J = 8.61 and 3.52 Hz, 1H), 7.42 (dd, J = 8.61 and 8.22 Hz, 1H), 7.34 (d, J = 8.22 Hz, 2H), 4.58 (s, 2H), 3.82 (d, J = 2.74 Hz, 2H), 3.68 (s, 2H), 2.67-2.55 (m, 5H), 1.64-1.54 (m, 4H), 1.44-1.84 (m, 2H), 1.83-1.75 (m, 2H), 1.64-1.57 (m, 4H), 1.47-1.37 (m, 2H), 1.00-0.95 (m, 4H). | 4A, 7D |
| 62 | 3-Cyclopropyl-1-(4-(6-(piperidin-1-ylmethyl)pyridin-2-yl)benzyl)imidazolidine-2,4-dione<br>$^1$H NMR (400 MHz, CDCl$_3$): δ 7.98 (d, J = 8.22 Hz, 2H), 7.72 (dd, J = 7.83 and 7.43 Hz, 1H), 7.56 (d, J = 7.83 Hz, 1H), 7.43 (d, J = 7.43 Hz, 1H), 7.34 (d, J = 8.22 Hz, 2H), 4.59 (s, 2H), 3.72 (s, 2H), 3.67 (s, 2H), 2.66-2.60 (m, 1H), 2.54-2.46 (m, 4H), 1.65-1.57 (m, 2H), 1.50-1.42 (m, 2H), 1.00-0.96 (m, 4H). | 4A, 5 |
| 63 | 3-Cyclopropyl-1-(4-(5-fluoro-6-((tetrahydro-2H-pyran-4-ylamino)methyl)pyridin-2-yl)benzyl)imidazolidine-2,4-dione<br>$^1$H NMR (400 MHz, CDCl$_3$): δ 7.95 (d, J = 8.22 Hz, 2H), 7.62 (dd, J = 8.61 and 3.51 Hz, 1H), 7.43 (dd, J = 9.00 and 8.61 Hz, 1H), 7.35 (d, J = 8.22 Hz, 2H), 4.59 (s, 2H), 4.09 (d, J = 1.96 Hz, 2H), 4.04-3.97 (m, 2H), 3.70 (s, 2H), 3.42 (Td, J = 11.74 and 2.35 Hz, 2H), 2.84-2.74 (m, 1H), 2.67-2.60 (m, 1H), 1.95-1.87 (m, 2H), 1.61-1.49 (m, 2H), 0.99-0.96 (m, 4H). | 4A, 7I |
| 64 | 3-Cyclopropyl-1-(4-(6-((tetrahydro-2H-pyran-4-ylamino)methyl)pyridin-2-yl)benzyl)imidazolidine-2,4-dione<br>$^1$H NMR (400 MHz, CDCl$_3$): δ 7.99 (d, J = 8.61 Hz, 2H), 7.72 (dd, J = 7.83 and 7.43 Hz, 1H), 7.59 (d, J = 7.83 Hz, 1H), 7.36 (d, J = 8.61 Hz, 2H), 7.26 (d, J = 7.43 Hz, 1H), 4.59 (s, 2H), 4.04-3.97 (m, 4H), 3.69 (s, 2H), 3.42 (Td, J = 11.74 and 1.96 Hz, 2H), 2.84-2.74 (m, 1H), 2.67-2.59 (m, 1H), 1.95-1.87 (m, 2H), 1.55-1.44 (m, 2H), 0.98-0.95 (m, 4H). | 4A, 6H |
| 65 | 3-Cyclopropyl-1-(4-(6-(1,1-dioxo-1$\lambda^6$-thiomorpholin-4-ylmethyl)pyridin-2-yl)benzyl)imidazolidine-2,4-dione<br>$^1$H NMR (400 MHz, CDCl$_3$): δ 7.98 (d, J = 8.22 Hz, 2H), 7.77 (dd, J = 7.83 and 7.43 Hz, 1H), 7.63 (d, J = 7.83 Hz, 1H), 7.36 (m, 3H), 4.59 (s, 2H), 3.92 (s, 2H), 3.69 (s, 2H), 3.18-3.08 (m, 8H), 2.67-2.59 (m, 1H), 0.98 (m, 4H). | 4A, 6$^a$ |
| 66 | 3-Cyclopropyl-1-(4-(6-(1,1-dioxo-1$\lambda^6$-thiomorpholin-4-ylmethyl)-5-fluoro-pyridin-2-yl)benzyl)imidazolidine-2,4-dione<br>$^1$H NMR (400 MHz, CDCl$_3$): δ 7.93 (d, J = 8.22 Hz, 2H), 7.68 (dd, J = 7.83 and 7.43 Hz, 1H), 7.63 (dd, J = 9.00 and 3.52 Hz, 1H), 7.36 (d, J = 8.22 Hz, 2H), 4.59 (s, 2H), 4.02 (s, 2H), 3.70 (s, 2H), | 4A, 7$^a$ |

| | Examples | Starting materials |
|---|---|---|
| | 3.24-3.19 (m, 4H), 3.13-3.07 (m, 4H), 2.67-2.59 (m, 1H), 1.01-0.96 (m, 4H). | |
| 67 | 3-Cyclobutyl-1-(4-(6-(piperidin-1-ylmethyl)pyridin-2-yl)benzyl)imidazolidine-2,4-dione<br>$^1$H NMR (400 MHz, CDCl$_3$): δ 7.98 (d, J = 8.22 Hz, 2H), 7.72 (dd, J = 7.83 and 7.43 Hz, 1H), 7.56 (d, J = 7.83 Hz, 1H), 7.43 (d, J = 7.43 Hz, 1H), 7.34 (d, J = 8.22 Hz, 2H), 4.63-4.53 (m, 3H), 3.72 (s, 2H), 3.67 (s, 2H), 2.97-2.84 (m, 2H), 2.54-2.46 (m, 4H), 2.24-2.14 (m, 2H), 1.92-1.82 (m, 1H), 1.79-1.67 (m, 1H), 1.65-1.57 (m, 4H), 1.52-1.40 (m, 2H). | 4B, 5 |
| 68 | 3-Cyclobutyl-1-(4-(5-fluoro-6-(piperidin-1-ylmethyl)pyridin-2-yl)benzyl)imidazolidine-2,4-dione<br>$^1$H NMR (400 MHz, CDCl$_3$): δ 7.96 (d, J = 8.22 Hz, 2H), 7.61 (dd, J = 8.61 and 3.52 Hz, 1H), 7.42 (dd, J = 9.00 and 8.61 Hz, 1H), 7.34 (d, J = 8.22 Hz, 2H), 4.59 (s, 2H), 3.83 (s, 2H), 3.68 (s, 2H), 2.96-2.85 (m, 2H), 2.63-2.54 (m, 4H), 2.24-2.13 (m, 2H), 1.92-1.82 (m, 1H), 1.78-1.67 (m, 1H), 1.64-1.56 (m, 4H), 1.45-1.37 (m, 2H). | 4B, 7D |
| 69 | 3-Cyclobutyl-1-(4-(5-fluoro-6-((tetrahydro-2H-pyran-4-ylamino)methyl)pyridin-2-yl)benzyl)imidazolidine-2,4-dione<br>$^1$H NMR (400 MHz, CDCl$_3$): δ 7.95 (d, J = 8.22 Hz, 2H), 7.61 (dd, J = 8.61 and 3.52 Hz, 1H), 7.42 (dd, J = 9.00 and 8.61 Hz, 1H), 7.35 (d, J = 8.22 Hz, 2H), 4.64-4.53 (m, 3H), 4.08 (bs, 2H), 4.04-3.97 (m, 2H), 3.69 (s, 2H), 3.42 (td, 11.74 and 1.96 Hz, 2H), 2.96-2.83 (m, 2H), 2.83-2.73 (m, 1H), 2.25-2.13 (m, 2H), 1.96-1.82 (m, 3H), 1.78-1.67 (m, 1H), 1.61-1.59 (m, 2H). | 4B, 7I |
| 70 | 3-Cyclobutyl-1-(4-(6-((tetrahydro-2H-pyran-4-ylamino)methyl)pyridin-2-yl)benzyl)imidazolidine-2,4-dione<br>$^1$H NMR (400 MHz, CDCl$_3$): δ 8.00 (d, J = 8.22 Hz, 2H), 7.72 (dd, J = 7.83 and 7.43 Hz, 1H), 7.42 (d, J = 7.83 Hz, 1H), 7.36 (d, J = 8.22 Hz, 2H), 7.25 (d, J = 7.43 Hz, 1H), 4.63-4.53 (m, 3H), 4.05-3.96 (m, 4H), 3.69 (s, 2H), 3.42 (td, 11.74 and 2.35 Hz, 2H), 2.96-2.84 (m, 2H), 2.83-2.74 (m, 1H), 2.24-2.14 (m, 2H), 1.95-1.82 (m, 3H), 1.77-1.67 (m, 1H), 1.58-1.46 (m, 2H). | 4B, 6H |
| 71 | 3-Cyclobutyl-1-(4-(6-(1,1-dioxo-1λ$^6$-thiomorpholin-4-ylmethyl)-5-fluoro-pyridin-2-yl)benzyl)imidazolidine-2,4-dione<br>$^1$H NMR (400 MHz, DMSO): δ 8.05 (d, J = 8.22, 2H), 7.99 (dd, J = 8.61 and 3.52 Hz, 1H), 7.81 (dd, J = 9.39 and 8.61 Hz, 1H), 7.40 (d, J = 8.22 Hz, 2H), 4.53 (s, 2H), 4.51-4.40 (m, 1H), 3.96 (bs, 2H), 3.86 (s, 2H), 3.15-3.01 (m, 8H), 2.83-2.71 (m, 2H), 2.15-2.04 (m, 2H), 1.77-1.65 (m, 2H). | 4B, 7$^a$ |
| 72 | 3-Cyclobutyl-1-(4-(6-(1,1-dioxo-1λ$^6$-thiomorpholin-4-ylmethyl)pyridin-2-yl)benzyl)imidazolidine-2,4-dione<br>$^1$H NMR (400 MHz, CDCl$_3$): δ 7.98 (d, J = 8.22 Hz, 2H), 7.77 (dd, J = 7.83 and 7.43 Hz, 1H), 7.63 (d, J = 7.83 Hz, 1H), 7.39-7.32 (m, 3H), 4.64-4.52 (m, 3H), 3.93 (s, 2H), 3.86 (s, 2H), 3.19-3.08 (m, 8H), 2.96-2.85 (m, 2H), 2.25-2.14 (m, 2H), 1.93-1.82 (m, 1H), 1.78-1.66 (m, 1H). | 4B, 6$^a$ |
| 73 | 1-(4-(6-(Piperidin-1-ylmethyl)pyridin-2-yl)benzyl)-3-(2,2,2-trifluoroethyl)imidazolidine-2,4-dione<br>$^1$H NMR (400 MHz, CDCl$_3$): δ 8.00 (d, J = 8.22 Hz, 2H), 7.73 (dd, J = 7.83 and 7.43 Hz, 1H), 7.56 (d, J = 7.83 Hz, 1H), 7.44 (d, J = 7.43 Hz, 1H), 7.35 (d, J = 8.22 Hz, 2H), 4.64 (s, 2H), 4.17 (q, J = 8.61 Hz, 2H), 3.84 (s, 2H), 3.72 (s, 2H), 2.54-2.46 (m, 4H), 1.67-1.56 (m, 4H), 1.51-1.42 (m, 2H). | 4C, 5 |
| 74 | 1-(4-(6-((3,3-Dimethylpiperidin-1-yl)methyl)-5-fluoropyridin-2-yl)benzyl)-3-(2,2,2-trifluoroethyl)imidazolidine-2,4-dione<br>$^1$H NMR (400 MHz, CDCl$_3$): δ 7.96 (d, J = 8.61 Hz, 2H), 7.61 (dd, J = 8.61 and 3.52 Hz, 1H), 7.41 (dd, J = 9.00 and 8.61 Hz, 1H), 7.35 (d, J = 8.61 Hz, 2H), 4.61 (s, 2H), 3.79 (d, J = 2.35 Hz, 2H), 4.08 (d, J = 2.75 Hz, 2H), 4.04-3.98 (m, 2H), 3.87 (s, 2H), 3.74 (s, 2H), 3.61 (q, J = 7.04 Hz, 2H), 2.49 (bs, 2H), 2.19 (bs, 2H), 1.64-1.55 (m, 2H), 1.27-1.22 (t, J = 7.04 Hz, 3H), 1.21-1.16 (m, 2H), 0.93 (s, 6H). | 4C, 7E |
| 75 | 1-(4-(5-Fluoro-6-(piperidin-1-ylmethyl)pyridin-2-yl)benzyl)-3-(2,2,2-trifluoro-ethyl)imidazolidine-2,4-dione<br>$^1$H NMR (400 MHz, CDCl$_3$): δ 7.98 (d, J = 8.22 Hz, 2H), 7.63 (dd, J = 8.21 and 3.52 Hz, 1H), 7.43 (dd, J = 9.00 and 8.61 Hz, 1H), 7.35 (d, J = 8.22 Hz, 2H), 4.64 (s, 2H), 4.19 (d, J = 8.61 Hz, 1H), 4.15 (d, J = 8.61 Hz, 1H), 3.87-3.82 (m, 4H), 2.64-2.54 (m, 4H), 1.65-1.56 (m, 4H), 1.46-1.37 (m, 2H). | 4C, 7D |
| 76 | 1-(4-(6-(1,1-Dioxo-1λ$^6$-thiomorpholin-4-ylmethyl)pyridin-2-yl)benzyl)-3-(2,2,2-trifluoro-ethyl)imidazolidine-2,4-dione<br>$^1$H NMR (400 MHz, CDCl$_3$): δ 8.00 (d, J = 8.22 Hz, 2H), 7.77 (dd, J = 7.83 and 7.43 Hz, 1H), 7.64 (d, J = 7.83 Hz, 1H), 7.41-7.34 (m, 3H), 4.65 (s, 2H), 4.20 (d, J = 8.22 Hz, 1H), 4.15 (d, J = 8.22 Hz, 1H), 3.93 (s, 2H), 3.85 (m, 2H), 3.20-3.08 (m, 8H). | 4C, 6$^a$ |

| | Examples | Starting materials |
|---|---|---|
| 77 | 1-(4-(6-(1,1-Dioxo-1λ⁶-thiomorpholin-4-ylmethyl)-5-fluoro-pyridin-2-yl)benzyl-3-(2,2,2-trifluoro-ethyl)imidazolidine-2,4-dione<br>¹H NMR (400 MHz, CDCl₃): δ 7.96 (d, J = 8.22 Hz, 2H), 7.69 (dd, J = 7.83 and 7.43 Hz, 1H), 7.49 (d, J = 7.83 Hz, 1H), 7.37 (d, J = 8.22 Hz, 2H), 4.65 (s, 2H), 4.20 (d, J = 8.22 Hz, 1H), 4.15 (d, J = 8.22 Hz, 1H), 4.02 (d, J = 2.35 Hz, 2H), 3.86 (s, 2H), 3.25-3.18 (m, 4H), 3.13-3.06 (m, 4H). | 4C, 7ᵃ |
| 78 | 1-(4-(6-((Tetrahydro-2H-pyran-4-ylamino)methyl)pyridin-2-yl)benzyl)-3-(2,2,2-trifluoro-ethyl)imidazolidine-2,4-dione<br>¹H NMR (400 MHz, CDCl₃): δ 8.02 (d, J = 8.22 Hz, 2H), 7.73 (dd, J = 7.83 and 7.43 Hz, 1H), 7.60 (d, J = 7.83 Hz, 1H), 7.37 (d, J = 8.22 Hz, 2H), 7.22 (d, J = 7.43 Hz, 1H), 4.65 (s, 2H), 4.20 (d, J = 8.22 Hz, 1H), 4.15 (d, J = 8.22 Hz, 1H), 4.03-3.96 (m, 4H), 3.85 (s, 2H), 3.41 (td, J = 11.74 and 2.35 Hz, 2H), 2.85-2.75 (m, 1H), 1.96-1.86 (m, 2H), 1.54-1.47 (m, 2H). | 4C, 6H |
| 79 | 1-(4-(5-Fluoro-6-((tetrahydro-2H-pyran-4-ylamino)methyl)pyridin-2-yl)benzyl)-3-(2,2,2-trifluoro-ethyl)imidazolidine-2,4-dione<br>¹H NMR (400 MHz, CDCl₃): δ 7.97 (d, J = 8.22 Hz, 2H), 7.62 (dd, J = 7.83 and 7.43 Hz, 1H), 7.44 (dd, J = 9.00 and 8.61 Hz, 1H), 7.37 (d, J = 8.22 Hz, 2H), 4.65 (s, 2H), 4.20 (d, J = 8.61 Hz, 1H), 4.16 (d, J = 8.61 Hz, 1H), 4.08 (bs, 2H), 4.04-3.98 (m, 2H), 3.86 (s, 2H), 3.46 (td, J = 11.74 and 2.35 Hz, 2H), 2.83-2.73 (m, 1H), 1.95-1.88 (m, 2H), 1.60-1.49 (m, 2H). | 4C, 7I |
| 80 | 3-((R)-1-Cyclopropylethyl)-1-(4-(5-fluoro-6-(piperidin-1-ylmethyl)pyridin-2-yl)benzyl)imidazolidine-2,4-dione<br>¹H NMR (400 MHz, CDCl₃): δ 7.97 (d, J = 8.22 Hz, 2H), 7.63 (dd, J = 8.61 and 3.91 Hz, 1H), 7.43 (d, J = 9.00 and 8.61 Hz, 1H), 7.35 (d, J = 8.22 Hz, 2H), 4.60 (s, 2H), 3.83 (bs, 2H), 3.71 (s, 2H), 2.63-2.54 (m, 4H), 2.32-2.25 (m, 1H), 1.65-1.50 (m, 4H), 1.46-1.35 (m, 2H), 0.66-0.58 (m, 1H), 0.50-0.41 (m, 1H), 0.29-0.24 (m, 2H). | 4D, 7D |
| 81 | (S)-1-(4-(5-fluoro-6-(piperidin-1-ylmethyl)pyridin-2-yl)benzyl)-3-(1-methoxypropan-2-yl)imidazolidine-2,4-dione<br>¹H NMR (400 MHz, CDCl₃): δ 7.96 (d, J = 8.22 Hz, 2H), 7.62 (dd, J = 8.61 and 3.52 Hz, 1H), 7.42 (d, J = 9.00 and 8.61 Hz, 1H), 7.34 (d, J = 8.22 Hz, 2H), 4.62 (d, J = 14.87 Hz, 1H), 4.56 (d, J = 15.26 Hz, 1H), 4.49-4.39 (m, 1H) 3.95 (t, J = 9.78 Hz, 1H), 3.83 (d, J = 2.74 Hz, 2H), 3.71 (s, 2H), 3.45 (dd, J = 9.78 and 5.48 Hz, 1H), 3.35 (s, 3H), 2.62-2.35 (m, 4H), 1.63-1.54 (m, 4H), 1.46-1.34 (m, 5H). | 4E, 7D |
| 82 | 1-(4-(6-(Piperidin-1-ylmethyl)pyridin-2-yl)benzyl)-3-(tetrahydrofuran-3-yl)imidazolidine-2,4-dione<br>¹H NMR (400 MHz, CDCl₃): δ 7.99 (d, J = 8.22 Hz, 2H), 7.72 (dd, J = 7.83 and 7.43 Hz, 1H), 7.56 (d, J = 7.83 Hz, 1H), 7.43 (d, J = 7.43 Hz, 1H), 7.34 (d, J = 8.22 Hz, 2H), 4.80-4.71 (m, 1H), 4.59 (s, 32H), 4.20-4.11 (m, 1H), 4.05-3.85 (m, 3H), 3.72 (bs, 4H), 2.53-2.45 (m, 4H), 2.42-2.32 (m, 1H), 2.26-2.15 (m, 1H), 1.65-1.56 (m, 4H), 1.52-1.40 (m, 2H). | 4F, 5 |
| 83 | 1-(4-(5-Fluoro-6-(piperidin-1-ylmethyl)pyridin-2-yl)benzyl)-3-(tetrahydrofuran-3-yl)imidazolidine-2,4-dione<br>¹H NMR (400 MHz, CDCl₃): δ 7.96 (d, J = 8.22 Hz, 2H), 7.62 (dd, J = 8.61 and 3.52 Hz, 1H), 7.43 (dd, J = 9.00 and 8.61 Hz, 1H), 7.34 (d, J = 8.22 Hz, 2H), 4.81-4.70 (m, 1H), 4.60 (s, 2H), 4.20-4.12 (m, 1H), 4.05-3.85 (m, 3H), 3.83 (d, J = 2.74 Hz, 2H), 3.73 (s, 2H), 2.63-2.54 (m, 4H), 2.42-2.33 (m, 1H), 2.26-2.15 (m, 1H), 1.64-1.54 (m, 4H), 1.46-1.38 (m, 2H). | 4F, 7D |
| 84 | 1-(4-(5-Fluoro-6-((tetrahydro-2H-pyran-4-ylamino)methyl)pyridin-2-yl)benzyl)-3-(tetrahydro-furan-3-yl)imidazolidine-2,4-dione<br>¹H NMR (400 MHz, CDCl₃): δ 7.96 (d, J = 8.22 Hz, 2H), 7.62 (dd, J = 8.61 and 3.52 Hz, 1H), 7.43 (dd, J = 9.00 and 8.61 Hz, 1H), 7.36 (d, J = 8.22 Hz, 2H), 4.80-4.70 (m, 1H), 4.60 (s, 2H), 4.19-4.12 (m, 1H), 4.08 (d, J = 1.96 Hz, 2H), 4.04-3.86 (m, 5H), 3.74 (s, 2H), 3.42 (td, J = 11.74 and 1.96 Hz, 2H), 2.84-2.73 (m, 1H), 2.43-2.32 (m, 1H), 2.25-2.15 (m, 1H), 1.95-1.87 (m, 2H), 1.61-1.47 (m, 2H). | 4F, 7I |
| 85 | 3-Cyclobutyl-1-(4-(5-fluoro-6-(thiomorpholinomethyl)pyridin-2-yl)benzyl)imidazolidine-2,4-dione<br>¹H NMR (400 MHz, CDCl₃): δ 7.95 (d, J = 8.22 Hz, 2H), 7.64 (dd, J = 8.61 and 3.52 Hz, 1H), 7.44 (dd, J = 9.00 and 8.61 Hz, 1H), 7.35 (d, J = 8.61 Hz, 2H), 4.59-4.53 (m, 3H), 3.88 (d, J = 2.35 Hz, 2H), 3.68 (s, 2H), 2.96-2.85 (m, 6H), 2.72-2.68 (m, 4H), 2.24-2.14 (m, 1H), 1.92-1.81 (m, 1H), 1.78-1.67 (m, 1H). | 4B, 7L |
| 86 | 3-Cyclobutyl-1-(4-(6-(thiomorpholinomethyl)pyridin-2-yl)benzyl)imidazolidine-2,4-dione<br>¹H NMR (400 MHz, CDCl₃): δ 7.98 (d, J = 8.22 Hz, 2H), 7.73 (dd, J = 7.83 and 7.43 Hz, 1H), 7.58 (d, J = 7.83 Hz, 1H), 7.40 (d, J = 7.43 Hz, 1H), 7.35 (d, J = 8.22 Hz, 2H), 4.61-4.55 (m, 3H), 3.78 | 4B, 6K |

| Examples | Starting materials |
|---|---|
| (s, 2H), 3.67 (s, 2H), 2.94-2.82 (m, 6H), 2.75-2.69 (m, 4H), 2.24-2.14 (m, 2H), 1.92-1.80 (m, 1H), 1.80-1.68 (m, 1H). | |
| 87 1-(4-(5-Fluoro-6-(thiomorpholinomethyl)-pyridin-2-yl)benzyl)-3-propylimidazolidine-2,4-dione<br>$^1$H NMR (400 MHz, CDCl$_3$): δ 7.95 (d, J = 8.61 Hz, 2H), 7.64 (dd, J = 8.61 and 3.52 Hz, 1H), 7.44 (dd, J = 9.00 and 8.61 Hz, 1H), 7.35 (d, J = 8.61 Hz, 2H), 4.62 (s, 2H), 3.89 (d, J = 2.35 Hz, 2H), 3.75 (s, 2H), 3.54-3.49 (m, 2H), 2.95-2.89 (m, 4H), 2.73-2.68 (m, 4H), 1.74-1.61 (m, 2H), 0.95 (t, J = 7.43 Hz, 3H). | 2C, 7L |
| 88 3-Propyl-1-(4-(6-(thiomorpholinomethyl)pyridin-2-yl)benzyl)imidazolidine-2,4-dione<br>$^1$H NMR (400 MHz, CDCl$_3$): δ 7.98 (d, J = 8.22 Hz, 2H), 7.73 (dd, J = 7.83 and 7.43 Hz, 1H), 7.58 (d, J = 7.83 Hz, 1H), 7.40 (d, J = 7.43 Hz, 1H), 7.35 (d, J = 8.22 Hz, 2H), 4.62 (s, 2H), 3.78 (d, J = 2.35 Hz, 2H), 3.73 (s, 2H), 3.54-3.48 (m, 2H), 2.86-2.82 (m, 4H), 2.75-2.68 (m, 4H), 1.74-1.62 (m, 2H), 0.94 (t, J = 7.43 Hz, 3H). | 2C, 6K |

EXAMPLE 89

1-(4-(6-(Piperidin-1-ylmethyl)pyridin-2-yl)benzyl)imidazolidine-2,4-dione

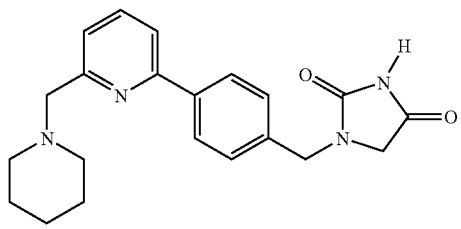

i) To a solution of 2-bromo-6-piperidin-1-ylmethyl-pyridine (example 5) (8.0 g, 31.4 mmol) and 4-formylphenylboronic acid (6.1 g, 40.8 mmol) in toluene/ethanol (4/1, 320 ml) was added an aqueous solution of 2M potassium carbonate. After 15 minutes stirring under a nitrogen atmosphere, tetrakis(triphenylphosphine)palladium(0) (1.2 g, 1.02 mmol) was added. After stirring for 17 h at 80° C. under a nitrogen atmosphere, the mixture was cooled to room temperature and filtered through decalite. Water was added and the product was extracted into ethylacetate. The combined organic phases were washed with water, brine, dried over sodium sulfate and concentrated under reduced pressure. Column chromatography afforded 4-(6-(piperidin-1-ylmethyl)pyridin-2-yl)benzaldehyde (7.69 g) as a white solid.

ii) A solution of glycine methylester.HCl (4.79 g, 38.1 mmol) and triethylamine 4.60 ml, 33.0 mmol) in methanol (70 ml) was added dropwise to a solution of the product obtained in the previous step (7.12 g, 25.4 mmol) in methanol (70 ml) under a nitrogen atmosphere. After stirring for 1 h at room temperature, sodium sodium triacetoxyborohydride (12.9 g, 61.0 mmol) was added portion wise during a 30 minutes period of time. After 17 h stirring more glycine methylester.HCl (1.6 g, 12.7 mmol) was added, followed by addition of sodium triacetoxyborohydride (5.38 g, 25.4 mmol). After stirring for another 17 h the reaction mixture was quenched by the addition of a saturated aqueous solution of sodium hydrogen carbonate. The product was extracted into dichloromethane and the combined organic phases were washed with water, brine, filtered through a phase separation filtered and concentrated under reduced pressure. Column chromatography afforded methyl 2-(4-(6-(piperidin-1-ylmethyl)pyridin-2-yl)benzylamino)acetate (3.48 g) as a white solid.

iii) To a suspension of the product obtained in the previous step (8.03 g, 22.7 mmol) in dioxane/water (1/1) (100 ml) was added at room temperature, potassium cyanate (2.76 g, 34.1 mmol). After 20 minutes stirring, acetic acid (4.16 ml, 72.7 mmol) was added and the mixture was stirred for another 17 h at room temperature. The reaction mixture was quenched by the addition of water and basified by the addition of a saturated aqueous solution of sodium hydrogen carbonate until pH=9. The product was extracted into dichloromethane and the combined organic phases were washed with brine, filtered through a phase separation filter and concentrated under reduced pressure to afford methyl 2-(1-(4-(6-(piperidin-1-ylmethyl)pyridin-2-yl)benzyl)ureido)acetate (8.2 g) as an oil. The product was used in the following step without further purification.

iv) To a solution of the product obtained in the previous step (8.2 g, 20.68 mmol) in methanol (50 ml) was added at room temperature, sodium methoxide (2.24 g, 41.4 mmol) and the reaction mixture was stirred for 3 h at room temperature under a nitrogen atmosphere. The reaction mixture was poured into water and neutralized by the addition of a saturated aqueous solution of ammonium chloride. The product was extracted into dichloromethane and the combined organic phases were washed with brine, dried over sodium sulfate and concentrated under reduced pressure. Column chromatography afforded the title compound 1-(4-(6-(piperidin-1-ylmethyl)pyridin-2-yl)benzyl)imidazolidine-2,4-dione (5.8 g) as a white solid.

1H NMR (400 MHz, CDCl3): δ 7.99 (d, J=8.61 Hz, 2H), 7.72 (dd, J=7.83 and 7.43 Hz, 1H), 7.57 (d, J=7.83 Hz, 1H), 7.42 (d, J=7.43 Hz, 1H), 7.34 (d, J=8.61 Hz, 2H), 4.57 (s, 2H), 3.77 (s, 2H), 3.73 (s, 2H), 2.56-2.48 (m, 4H), 1.67-1.57 (m, 4H), 1.50-1.42 (m, 2H).

EXAMPLE 90

1-(4-(6-(Piperidin-1-ylmethyl)pyridin-2-yl)benzyl)-3-(3,3,3-trifluoro-propyl)imidazolidine-2,4-dione

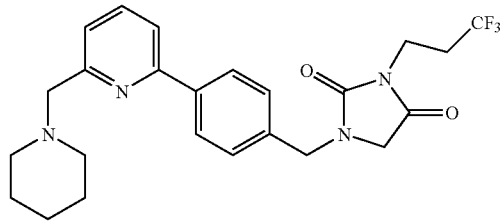

i) A solution of 1-(4-(6-Piperidin-1-ylmethyl-pyridin-2-yl) benzyl)imidazolidine-2,4-dione (example 134) (120 mg, 0.33 mmol), potassium carbonate (137 mg, 0.99 mmol) and 3-bromo-1,1,1-trifluoropropane (117 mg, 0.66 mmol) in DMF (2.5 ml) was stirred during 17 h at 50° C. After cooling to room temperature the reaction mixture was quenched by the addition of water. The product was extracted into ethylacetate and the combined organic phases were washed with brine, dried over sodium sulfate and concentrated under reduced pressure. Column chromatography afforded the title compound (50 mg) as a white solid.

1H NMR (400 MHz, CDCl3): δ 7.99 (d, J=8.61 Hz, 2H), 7.72 (dd, J=7.83 and 7.43 Hz, 1H), 7.56 (d, J=7.83 Hz, 1H), 7.44 (d, J=7.43 Hz, 1H), 7.33 (d, J=8.61 Hz, 2H), 4.62 (s, 2H), 3.83 (t, J=7.04 Hz, 2H), 3.76 (s, 2H), 3.73 (s, 2H), 2.60-2.45 (m, 6H), 1.66-1.59 (m, 4H), 1.51-1.41 (m, 2H).

EXAMPLE 91

Following a procedure analogous to that described in Example 90 the following compounds were prepared.

91A: 4-(2,5-Dioxo-3-(4-(6-(piperidin-1-ylmethyl) pyridin-2-yl)benzyl)imidazolidin-1-yl)butanenitrile 1H NMR (400 MHz, CDCl3): δ 8.00 (d, J=8.61 Hz, 2H), 7.72 (dd, J=7.83 and 7.43 Hz, 1H), 7.56 (d, J=7.83 Hz, 1H), 7.43 (d, J=7.43 Hz, 1H), 7.35 (d, J=8.61 Hz, 2H), 4.62 (s, 2H), 3.78 (s, 2H), 3.72 (s, 2H), 3.69 (t, J=6.65 Hz, 2H), 2.54-2.47 (m, 4H), 2.44 (t, J=7.04 Hz, 2H), 2.05 (m, 2H), 1.65-1.56 (m, 4H), 1.50-1.40 (m, 2H).

91B: (R)-methyl 3-(2,5-dioxo-3-(4-(6-(piperidin-1-ylmethyl)pyridin-2-yl)benzyl)imidazolidin-1-yl)-2-methylpropanoate 1H NMR (400 MHz, CDCl3): δ 7.99 (d, J=8.22 Hz, 2H), 7.72 (dd, J=7.83 and 7.43 Hz, 1H), 7.56 (d, J=7.83 Hz, 1H), 7.43 (d, J=7.43 Hz, 1H), 7.34 (d, J=8.22 Hz, 2H), 4.61 (s, 2H), 3.83 (dd, J=13.69 and 7.83 Hz, 1H), 3.75 (s, 2H), 3.72 (s, 2H), 3.69 (s, 3H), 3.63 (dd, J=14.09 and 6.65 Hz, 1H), 3.00-2.90 (m, 1H), 2.54-2.46 (m, 4H), 1.65-1.54 (m, 4H), 1.51-1.41 (m, 2H), 1.20 (d, J=7.04 Hz, 3H).

91C: 3-(Oxetan-2-ylmethyl)-1-(4-(6-(piperidin-1-ylmethyl)pyridin-2-yl)benzyl)imidazolidine-2,4-dione 1H NMR (400 MHz, CDCl3): δ 7.99 (d, J=8.61 Hz, 2H), 7.72 (dd, J=7.83 and 7.43 Hz, 1H), 7.56 (d, J=7.83 Hz, 1H), 7.43 (d, J=7.43 Hz, 1H), 7.34 (d, J=8.61 Hz, 2H), 5.08-5.00 (m, 1H), 4.70-4.56 (m, 4H), 3.99-3.93 (dd, J=14.08 and 7.43 Hz, 1H), 3.78-3.70 (m, 5H), 2.78-2.70 (m, 1H), 2.55-2.45 (m, 4H), 1.66-1.58 (m, 5H), 1.50-1.41 (m, 2H).

91D: 3-(2-Oxotetrahydrofuran-3-yl)-1-(4-(6-(piperidin-1-ylmethyl)pyridin-2-yl)benzyl)imidazolidine-2,4-dione 1H NMR (400 MHz, CDCl3): δ 8.00 (d, J=8.61 Hz, 2H), 7.73 (dd, J=7.83 and 7.43 Hz, 1H), 7.57 (d, J=7.83 Hz, 1H), 7.44 (d, J=7.43 Hz, 1H), 7.36 (d, J=8.61 Hz, 2H), 4.97-4.90 (m, 1H), 4.65-4.56 (m, 5H), 4.39-4.31 (m, 1H), 3.82 (s, 2H), 3.73 (s, 2H), 2.84-2.72 (m, 1H), 2.59-2.47 (m, 5H), 1.66-1.57 (m, 4H), 1.50-1.42 (m, 2H).

91E: 1-(4-(6-(Piperidin-1-ylmethyl)pyridin-2-yl) benzyl)-3-(tetrahydrofuran-2-yl)imidazolidine-2,4-dione 1H NMR (400 MHz, CDCl3): δ 7.99 (d, J=8.22 Hz, 2H), 7.72 (dd, J=7.83 and 7.43 Hz, 1H), 7.56 (d, J=7.83 Hz, 1H), 7.43 (d, J=7.43 Hz, 1H), 7.34 (d, J=8.22 Hz, 2H), 4.65 (d, J=15.26 Hz, 1H), 4.58 (d, J=15.26 Hz, 1H), 4.30-4.22 (m, 1H), 3.96-3.88 (m, 1H), 3.81-3.64 (m, 6H), 3.50 (dd, J=13.69 and 4.70 Hz, 1H), 2.55-2.45 (m, 4H), 2.08-1.84 (m, 3H), 1.72-1.57 (m, 5H), 1.50-1.42 (m, 2H).

EXAMPLE 92

2-Amino-N-cyclopropylacetamide trifluoroacetate i) TBTU (5.1 g, 16.5 mmol), DIPEA (2.9 ml, 16.5 mmol) and cyclopropylamine (2.2 ml, 33 mmol) were added to a solution of BOC-Gly-OH (2.63 g, 15 mmol) in dry dichloromethane (10 ml). After 17 h stirring, the reaction mixture was concentrated under reduced pressure and water was added to the residue. The product was extracted into ethyl acetate. The combined organic phases were washed with an aqueous solution of 2M hydrochloric acid, a saturated aqueous solution of sodium hydrogen carbonate, brine, dried over sodium sulfate and concentrated under reduced pressure to give 2-tert-butyl 2-(cyclopropylamino)-2-oxoethylcarbamate (847 mg). The product was used in the following step without further purification.

ii) TFA (65 ml, 875 mmol) was added to a solution of the product obtained in the previous step (34.9 g, 163 mmol) in dichloromethane (300 ml). After 17 h stirring the reaction mixture was concentrated under reduced pressure. Crystallization from DCM/diisopropyletherether afforded the title compound 2-Amino-N-cyclopropylacetamide trifluoroacetate (22.2 g). 1H NMR (400 MHz, MeOD): δ 3.62 (s, 2H), 2.76-2.74 (m, 1H), 0.75 (m, 2H), 0.52 (m, 2H)

EXAMPLE 93

3-Cyclopropyl-1-(3-fluoro-4-(5-fluoro-6-(piperidin-1-ylmethyl)pyridin-2-yl)benzyl)imidazolidine-2,4-dione i) 3-Fluoro-4-(5-fluoro-6-(piperidin-1-ylmethyl)pyridin-2-yl)benzaldehyde was prepared following a procedure analogous to that described in Example 89, step i), using 2-fluoro-4-formylphenylboronic acid as the starting material.

ii) To a solution of the product obtained in the previous step (1.3 g, 4.1 mmol) in methanol (60 ml) were added at 0° C. KOH (4.6 mg, 0.08 mmol) and 2-amino-N-cyclopropyl-acetamide trifluoroacetate (1.9 g, 8.22 mmol). After 30 minutes at 0° C. sodium triacetoxy borohydride (2.6 g, 12.3 mmol) was added. After 17 h stirring at room temperature the reaction mixture was quenched by addition of a saturated aqueous solution of sodium hydrogen carbonate and the product was extracted into dichloromethane. The combined organic phases were washed with water, brine, dried over sodium sulphate and concentrated under reduced pressure. Column chromatography afforded N-cyclopropyl-2-(3-fluoro-4-(5-fluoro-6-(piperidin-1-ylmethyl)pyridin-2-yl)benzylamino) acetamide (0.6 g).

iii) Following a procedure analogous to that described in Example 3, step iii), the product obtained in the previous step (0.28 g), was converted to the title compound 3-Cyclopropyl- 1-(3-fluoro-4-(5-fluoro-6-(piperidin-1-ylmethyl)pyridin-2-yl)benzyl)imidazolidine-2,4-dione (43 mg).

$^1$H NMR (400 MHz, CDCl$_3$): δ 8.00 (dd, J=8.22 and 7.83 Hz, 1H), 7.74-7.68 (m, 1H), 7.43 (dd, J=9.00 and 8.61 Hz, 1H), 7.15 (dd, J=8.22 and 1.96 Hz, 1H), 7.06 (dd, J=11.74 and 1.57 Hz, 1H), 4.57 (s, 2H), 3.81 (d, J=2.35 Hz, 2H), 3.71 (s, 2H), 2.68-2.53 (m, 5H), 1.65-1.50 (m, 4H), 1.46-1.38 (m, 2H), 1.00 (s, 2H), 0.98 (s, 2H).

EXAMPLE 94

1-(3-Fluoro-4-(6-(piperidin-1-ylmethyl)pyridin-2-yl)benzyl)-3-isobutylimidazolidine-2,4-dione i) 3-Fluoro-4-(6-(piperidin-1-ylmethyl)pyridin-2-yl)benzaldehyde was prepared following a procedure analogous to that described in Example 89, step i), using 2-Fluoro-4-formylphenylboronic acid as the starting material.

ii) Following a procedure analogous to that described in Example 93, step ii), the product obtained in the previous step (1 g), was converted using glycinamide hydrochloric acid as the starting material to 2-(3-Fluoro-4-(6-(piperidin-1-ylmethyl)pyridin-2-yl)benzylamino)-acetamide (0.9 g).

iii) Following a procedure analogous to that described in Example 3, step iii), the product obtained in the previous step (0.9 g), was converted to 1-(3-Fluoro-4-(6-(piperidin-1-ylmethyl)pyridin-2-yl)benzyl)imidazolidine-2,4-dione (0.49 g).

iv) Following a procedure analogous to that described in Example 90, step i, the product obtained in the previous step (0.49 g), was converted to 1-(3-Fluoro-4-(6-(piperidin-1-ylmethyl)pyridin-2-yl)benzyl)-3-isobutylimidazolidine-2,4-dione (52 mg).

$^1$H NMR (400 MHz, CDCl$_3$): δ 8.00 (dd, J=8.22 and 7.83 Hz, 1H), 7.73 (dd, J=7.83 and 7.43 Hz, 1H), 7.65-7.60 (m, 1H), 7.46 (d, J=7.83 Hz, 1H), 7.14 (dd, J=7.83 and 1.57 Hz, 1H), 7.05 (dd, J=11.74 and 1.57 Hz, 1H), 4.60 (s, 2H), 3.77 (s, 2H), 3.71 (s, 2H), 3.37 (d, J=7.43 Hz, 2H), 2.53-2.45 (m, 4H), 2.14-2.06 (m, 1H), 1.65-1.57 (m, 4H), 1.50-1.42 (m, 2H), 0.94 (d, J=6.65 Hz, 6H).

EXAMPLE 95

Agonist Induced cAMP Change in Human CB2 Transfected CHO Cells

Adenylate cyclase assays were carried out using CHO cells stably over-expressing the human recombinant CB2 receptor. Cells were cultured in DMEM/HAMF12 containing 1% (v/v) penicillin/streptomycin (Gibco 15140-122), 10% Fetal Bovine Serum (FBS) and 400 µg/ml Geneticin (Invitrogen 10131-027). Compounds and reference (CP55,940) were dissolved in DMSO and dilutions were made in serum free medium containing 2 µM Rolipram (Sigma R6520) and 1 µM Forskolin (Sigma, F3917). 10 µl of each dilution was transferred to an assay plate (384-well white culture plate, Perkin Elmer). Cell suspensions containing 5×10$^5$ cells/ml in DMEM/HAMF12 containing 1% (v/v) penicillin/streptomycin were prepared from hCB2_C2-CHO cells and 10 µl (5,000 cells/well) thereof was transferred to the assay plate and cells were incubated for 45 min at 37° C. Homogeneous time-resolved fluorescence (HTRF; CisBio) was used as a read-out by sequentially adding 10 µl cAMP-XL665 and 10 µl anti-cAMP(Eu) cryptate; after 1 h incubation at room temperature, fluorescence at 615 nm and 665 nm was measured on Envision (Perkin Elmer). Results were calculated from the 665 nm/615 nm ratios obtained for individual compounds and were compared to values obtained for the reference compound. The compounds from Examples 12-88, 90, 91, 93 and 94 have an $EC_{50} \leq 1 \times 10^{-7}$ M for CB2.

EXAMPLE 95A

Agonist-Induced cAMP Change in Human CB1 Transfected CHO Cells

Adenylate cyclase assays were carried out using CHO cells stably over-expressing the human recombinant CB1 receptor. Cells were cultured in DMEM/HAMF12 containing 1% (v/v) penicillin/streptomycin (Gibco 15140-122), 10% Fetal Bovine Serum (FBS), 400 µg/ml Geneticin (Invitrogen 10131-027) and Zeocine 250 µg/ml (Invitrogen, 45-0430). Compounds and reference (CP55,940) were dissolved in DMSO and dilutions were made in serum free medium containing 2 µM Rolipram (Sigma R6520) and 1 µM Forskolin (Sigma, F3917). 10 µl of each dilution was transferred to an assay plate (384-well white culture plate, Perkin Elmer). Cell suspensions containing 5×10$^5$ cells/ml in DMEM/HAMF12 containing 1% (v/v) penicillin/streptomycin were prepared from hCB1_A2-CHO cells and 10 µl (5,000 cells/well) thereof was transferred to the assay plate and cells were incubated for 45 min at 37° C. Homogeneous time-resolved fluorescence (HTRF; CisBio) was used as a read-out by sequentially adding 10 µl cAMP-XL665 and 10 µl anti-cAMP (Eu) cryptate; after 1 h incubation at room temperature, fluorescence at 615 nm and 665 nm was measured on Envision (Perkin Elmer). Results were calculated from the 665 nm/615 nm ratios obtained for the individual compounds and were compared to values obtained for the reference compound. The compounds from Examples 12-88, 90, 91, 93 and 94 have an $EC_{50} \geq 1 \times 10^{-7}$ M for CB1.

EXAMPLE 96

The Rat (Chung) Model of Neuropathic Pain

In this model, mechanical allodynia is induced by tight ligation of the left L5 spinal nerve. This assay has been employed successfully to demonstrate anti-allodynic effects of anticonvulsants (gabapentin), antidepressants (duloxetine) and opioid analgesics (morphine) which are used clinically in the treatment of neuropathic pain.

Male Wistar rats (228-301 g body weight at time of surgery) were employed in the study. Rats were placed on an elevated (~40 cm) mesh floor in perspex boxes and the rats' withdrawal threshold to a mechanical stimulus (calibrated von Frey filaments) was measured using filaments of increasing force (2.6-167 mN) as described above. The von Frey filaments were applied to the plantar surface of the paw and threshold response determined using the up and down method. A positive response was noted if the paw was sharply withdrawn. A cut-off of 15 g was selected as the upper limit for testing. Following baseline measurements each animal was anaesthetised and the L5 spinal nerve tightly ligated. The animals were allowed to recover from the surgery for a period of at least three days. On the day of drug administration the paw withdrawal thresholds were re-measured (0 min). Immediately after this reading, the rats were dosed orally with vehicle or test compound and readings measured at various time points after compound administration.

Data were expressed as mean±s.e.m. Statistical analysis was performed using the Kruskal-Wallis one-way analysis of variance, a non-parametric statistical test. Each of the treatment groups were then compared against the vehicle group, using the non-parametric Dunn's test.

As an example, oral administration of the selective CB2 receptor agonist 3-isobutyl-1-(4-(6-(piperidin-1-ylmethyl)pyridin-2-yl)benzyl)imidazolidine-2,4-dione (Example 12) attenuated mechanical allodynia in a dose-dependent fashion (Table 1; FIG. 1) at 120 and 180 min post drug administration, respectively. The Minimum effective dose (MED) was 43.8 µmol/kg. These data demonstrate that selective CB2 receptor agonists posses potent oral anti-allodynic activity in a rat model of neuropathic pain.

TABLE 1

Effect of the compound of Example 12 on mechanical allodynia induced by spinal nerve ligation in rats.

| Route | Dose (µmol/kg) | Number of animals tested | Withdrawal threshold (g) at peak effect |
|---|---|---|---|
| Vehicle p.o. | 5 ml · kg$^{-1}$ | 7 | 1.10 ± 0.22 |
| 12 p.o. | 4.4 | 7 | 2.40 ± 0.64 |
| 12 p.o. | 13.2 | 7 | 4.32 ± 1.63 |
| 12 p.o. | 43.8 | 7 | 8.97 ± 2.21** |

Dose groups and number of animals per group.
*p ≦ 0.05
**p ≦ 0.01, Dunns test comparing vehicle-treated and compound-treated animals.

EXAMPLE 142

Mechanical Hyperalgesia in the Rat

In this rat model of inflammatory pain, inflammation is induced by subcutaneous injection of complete Freund's adjuvant (CFA) into the hind paw. The associated mechanical hyperalgesia is quantified by measuring the reduction in paw withdrawal threshold (PWT) to mechanical compression the paw. This assay has been employed successfully to demonstrate anti-hyperalgesic effects of non-steroidal anti-inflammatory drugs (indomethacin) and coxibs (celecoxib) which are used clinically in the treatment of inflammatory pain.

Experiments were conducted using male Wistar rats weighing (141-175 g). In brief, the rats' paw withdrawal threshold (PWT) to a mechanical compression of the hind paw was measured (baseline reading) using a Randall-Sellito apparatus (Ugo Basile). A cut-off of 20 g was employed to minimise tissue damage to the paw. The animals were then lightly anaesthetised with isoflurane (1-3%) and complete Freund's adjuvant (0.1 ml per paw) was injected subcutaneously (s.c.) into the plantar surface of the left hind paw. The animals were then returned to their home cage and left for the inflammation to develop. Twenty four hours after CFA injection, PWT's were re-measured (0 min) and immediately after this reading, rats were dosed orally with either vehicle or test compound (4.4-43.8 µmol/kg p.o. of compound 12). Readings were then made at 3 h post administration. Data were plotted as mean±s.e.m. and compared between groups using the Kruskal-Wallis one-way analysis of variance, a non-parametric statistical test. If statistical significance (P<0.05) was observed with this test, the vehicle group and each of the treatment groups were compared using the non-parametric Dunn's test. The percent attenuation of mechanical hyperalgesia is calculated as follows:

$$\% \text{ attenuation of hyperalgesia} = \frac{(\text{Post compound } PWT - \text{post } CFA\ PWT)}{(\text{Baseline } PWT - \text{post } CFA\ PWT)} \times 100$$

Oral administration of compound 12 (4.4-43.8 µmol/kg) reversed mechanical hyperalgesia induced by CFA in a dose-dependent fashion (Table 2). The MED for Org 266919-1 was 13.2 µmol/kg.

These data demonstrate that the selective CB2 receptor agonists possess potent oral anti-algesic activity in a rat model of inflammatory pain.

TABLE 2

Effect of compound 12 on mechanical hyperalgesia induced by complete Freund's adjuvant administered 24 h previously in rats.

| Route | Dose (µmol/kg) | Number of animals tested | % Attenuation of hyperalgesia (peak effect) |
|---|---|---|---|
| Vehicle p.o. | 5 ml · kg$^{-1}$ | 8 | −11.05 ± 12.27 |
| 12 p.o. | 4.4 | 8 | 58.64 ± 27.32 |
| 12 p.o. | 13.2 | 9 | 69.70 ± 12.88* |
| 12 p.o. | 43.8 | 8 | 116.74 ± 23.78** |

Dose groups and number of animals per group.
*p ≦ 0.01
**p ≦ 0.001, Dunns test comparing vehicle-treated and compound-treated animals.

The invention claimed is:

1. A 1-(4-(pyridin-2-yl)benzyl)imidazolidine-2,4-dione derivative having the Formula I

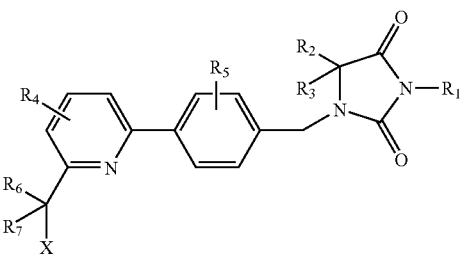

Formula I wherein $R_1$ is H, $(C_{1-6})$alkyl (optionally substituted with oxo, $(C_{1-3})$alkyloxy, $(C_{1-3})$-alkyloxycarbonyl, halogen or CN), $(C_{3-6})$cycloalkyl or $(C_{3-6})$cycloalkyl$(C_{1-3})$alkyl, each cycloalkyl ring optionally comprising a heteroatom selected from O and S;

$R_2$ and $R_3$ are independently H or $(C_{1-3})$alkyl; or $R_2$ and $R_3$ form together with the carbon atom to which they are bound a $(C_{3-5})$cycloalkyl group;

$R_4$ is H or 1 to 3 F substituents;

R$_5$ is H or 1 to 4 F substituents;
R$_6$ and R$_7$ are independently H or F;
X represents R$_8$, OR$_8$, NR$_8$R$_9$,

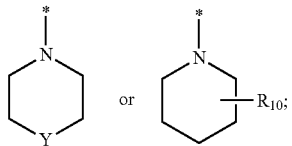

R$_8$ is (C$_{5-7}$)cycloalkyl optionally comprising a heteroatom selected from O, S, SO and SO$_2$;
R$_9$ is H or (C$_{1-4}$)alkyl;
R$_{10}$ represents 1-3 substituents independently selected from H, (C$_{1-3}$)alkyl, halogen, oxo, CN and CF$_3$;
Y is CF$_2$, O, S, SO or SO$_2$;
or a pharmaceutically acceptable salt thereof.

2. The 1-(4-(pyridin-2-yl)benzyl)imidazolidine-2,4-dione derivative of claim 1, wherein R$_2$, R$_3$ and R$_5$ are H.

3. The 1-(4-(pyridin-2-yl)benzyl)imidazolidine-2,4-dione derivative of claim 1, wherein R$_1$ is (C$_{1-4}$)alkyl.

4. The 1-(4-(pyridin-2-yl)benzyl)imidazolidine-2,4-dione derivative of claim 1, wherein X represents NR$_8$R$_9$,

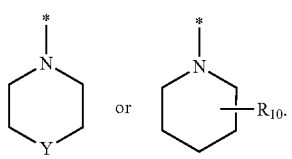

5. The 1-(4-(pyridin-2-yl)benzyl)imidazolidine-2,4-dione derivative of claim 4, wherein X is NR$_8$R$_9$ and R$_8$ is cyclohexyl optionally comprising a heteroatom selected from O and S.

6. The 1-(4-(pyridin-2-yl)benzyl)imidazolidine-2,4-dione derivative of claim 5, wherein R$_4$ is a F substituent at the position ortho to the CR$_6$R$_7$X group.

7. The 1-(4-(pyridin-2-yl)benzyl)imidazolidine-2,4-dione derivative of claim 1 which is selected from
3-Isobutyl-1-(4-(6-(piperidin-1-ylmethyl)pyridin-2-yl)benzyl)imidazolidine-2,4-dione;
3-isobutyl-1-(4-(6-(morpholinomethyl)pyridin-2-yl)benzyl)imidazolidine-2,4-dione;
1-(4-(5-Fluoro-6-((tetrahydro-2H-pyran-4-ylamino)methyl)pyridin-2-yl)benzyl)-3-isobutylimidazolidine-2,4-dione;
1-(4-(6-((1,1-Dioxo-1λ$^6$-thiomorpholin-4-yl)methyl)pyridin-2-yl)benzyl)-3-isobutylimidazolidine-2,4-dione;
1-(4-(6-((1,1-Dioxo-1λ$^6$-thiomorpholin-4-yl)methyl)-5-fluoropyridin-2-yl)benzyl)-3-isobutylimidazolidine-2,4-dione;
3-Isobutyl-1-(4-(6-((tetrahydro-2H-pyran-4-ylamino)methyl)pyridin-2-yl)benzyl)imidazolidine-2,4-dione;
3-Ethyl-1-(4-(6-(piperidin-1-ylmethyl)pyridin-2-yl)benzyl)imidazolidine-2,4-dione;
3-Ethyl-1-(4-(5-fluoro-6-(piperidin-1-ylmethyl)pyridin-2-yl)benzyl)imidazolidine-2,4-dione;
1-(4-(6-(1,1-Dioxo-1λ$^6$-thiomorpholin-4-ylmethyl)-5-fluoropyridin-2-yl)benzyl)-3-ethylimidazolidine-2,4-dione;
1-(4-(6-(1,1-dioxo-1λ$^6$-thiomorpholin-4-ylmethyl)pyridin-2-yl)benzyl)-3-ethylimidazolidine-2,4-dione;
1-(4-(5-Fluoro-6-((tetrahydro-2H-pyran-4-ylamino)methyl)pyridin-2-yl)benzyl)-3-propylimidazolidine-2,4-dione;
1-(4-(6-(1,1-Dioxo-1λ$^6$-thiomorpholin-4-ylmethyl)-5-fluoropyridin-2-yl)benzyl)-3-propylimidazolidine-2,4-dione;
3-(2,2-Difluoroethyl)-1-(4-(6-(piperidin-1-ylmethyl)pyridin-2-yl)benzyl)imidazolidine-2,4-dione;
3-(2,2-Difluoroethyl)-1-(4-(5-fluoro-6-(piperidin-1-ylmethyl)pyridin-2-yl)benzyl)imidazolidine-2,4-dione;
3-(Cyclopropylmethyl)-1-(4-(5-fluoro-6-(piperidin-1-ylmethyl)pyridin-2-yl)benzyl)imidazolidine-2,4-dione;
3-(Cyclopropylmethyl)-1-(4-(6-(piperidin-1-ylmethyl)pyridin-2-yl)benzyl)imidazolidine-2,4-dione;
3-(2-Oxopropyl)-1-(4-(6-(piperidin-1-ylmethyl)pyridin-2-yl)benzyl)imidazolidine-2,4-dione;
1-(4-(5-Fluoro-6-(piperidin-1-ylmethyl)pyridin-2-yl)benzyl)-3-(2-oxopropyl)imidazolidine-2,4-dione;
1-(4-(6-(1,1-Dioxo-1λ$^6$-thiomorpholin-4-ylmethyl)-5-fluoropyridin-2-yl)benzyl)-3-(2-oxopropyl)imidazolidine-2,4-dione;
3-Isopropyl-1-(4-(6-(piperidin-1-ylmethyl)pyridin-2-yl)benzyl)imidazolidine-2,4-dione;
1-(4-(6-(1,1-Dioxo-1λ$^6$-thiomorpholin-4-ylmethyl)-5-fluoropyridin-2-yl)benzyl)-3-isopropylimidazolidine-2,4-dione;
1-(4-(6-(1,1-Dioxo-1λ$^6$-thiomorpholin-4-ylmethyl)pyridin-2-yl)benzyl)-3-isopropylimidazolidine-2,4-dione;
3-Cyclopropyl-1-(4-(5-fluoro-6-(piperidin-1-ylmethyl)pyridin-2-yl)benzyl)imidazolidine-2,4-dione;
3-Cyclopropyl-1-(4-(6-(1,1-dioxo-1λ$^6$-thiomorpholin-4-ylmethyl)-5-fluoro-pyridin-2-yl)benzyl)imidazolidine-2,4-dione;
3-Cyclobutyl-1-(4-(5-fluoro-6-((tetrahydro-2H-pyran-4-ylamino)methyl)pyridin-2-yl)benzyl)imidazolidine-2, 4-dione;
3-Cyclobutyl-1-(4-(6-((tetrahydro-2H-pyran-4-ylamino)methyl)pyridin-2-yl)benzyl)imidazolidine-2,4-dione;
3-Cyclobutyl-1-(4-(6-(1,1-dioxo-1λ$^6$-thiomorpholin-4-ylmethyl)-5-fluoropyridin-2-yl)benzyl)imidazolidine-2,4-dione;
3-Cyclobutyl-1-(4-(6-(1,1-dioxo-1λ$^6$-thiomorpholin-4-ylmethyl)pyridin-2-yl)benzyl)imidazolidine-2,4-dione;
1-(4-(6-(Piperidin-1-ylmethyl)pyridin-2-yl)benzyl)-3-(2,2,2-trifluoroethyl)imidazolidine-2,4-dione;
1-(4-(6-(1,1-Dioxo-1λ$^6$-thiomorpholin-4-ylmethyl)-5-fluoropyridin-2-yl)benzyl-3-(2,2,2-trifluoroethyl)imidazolidine-2,4-dione;
1-(4-(6-((Tetrahydro-2H-pyran-4-ylamino)methyl)pyridin-2-yl)benzyl)-3-(2,2,2-trifluoroethyl)imidazolidine-2,4-dione; and
1-(4-(5-Fluoro-6-((tetrahydro-2H-pyran-4-ylamino)methyl)pyridin-2-yl)benzyl)-3-(2,2,2-trifluoroethyl)imidazolidine-2,4-dione; or a pharmaceutically acceptable salt thereof.

8. A pharmaceutical composition comprising a 1-(4-(pyridin-2-yl)benzyl)imidazolidine-2,4-dione derivative of claim 1 or a pharmaceutically acceptable salt thereof in admixture with one or more pharmaceutically acceptable auxilliaries.

9. A pharmaceutical composition comprising a 1-(4-(pyridin-2-yl)benzyl)imidazolidine-2,4-dione derivative of claim 7 or a pharmaceutically acceptable salt thereof in admixture with one or more pharmaceutically acceptable auxilliaries.

10. A method of treatment of pain comprising administering to a patient in need thereof a therapeutically effective amount of a 1-(4-(pyridin-2-yl)benzyl)imidazolidine-2,4-dione derivative of claim 1 or a pharmaceutically acceptable salt thereof.

11. The method of claim 10 wherein the pain is selected from the group consisting of peri-operative pain, chronic pain, neuropathic pain, cancer pain and pain and spasticity associated with multiple sclerosis.

12. A method of treatment of pain comprising administering to a patient in need thereof a therapeutically effective amount of a 1-(4-(pyridin-2-yl)benzyl)imidazolidine-2,4-dione derivative of claim 7 or a pharmaceutically acceptable salt thereof.

13. The method of claim 12 wherein the pain is selected from the group consisting of peri-operative pain, chronic pain, neuropathic pain, cancer pain and pain and spasticity associated with multiple sclerosis.

* * * * *